United States Patent [19]

Jezl et al.

[11] Patent Number: 4,968,655

[45] Date of Patent: Nov. 6, 1990

[54] CATALYSTS FOR CONVERSION OF A LOWER ALKANE

[75] Inventors: James L. Jezl, St. Charles; Glenn O. Michaels, South Holland; Michael J. Spangler, Dolton; Mark L Winzenburg, Naperville, all of Ill.

[73] Assignee: Amoco Corporation, Chicago, Ill.

[21] Appl. No.: 314,765

[22] Filed: Feb. 23, 1987

Related U.S. Application Data

[62] Division of Ser. No. 706,731, Feb. 19, 1985, Pat. No. 4,814,539.

[51] Int. Cl.$^5$ .......................... B01J 21/08; B01J 23/14
[52] U.S. Cl. .................................... 502/242; 502/241; 502/246; 502/250

[58] Field of Search ............... 502/235, 236, 238, 239, 502/241, 242, 247, 250

[56] References Cited

U.S. PATENT DOCUMENTS

| | | | |
|---|---|---|---|
| 2,330,090 | 9/1943 | Thomas et al. | 502/241 |
| 2,470,142 | 5/1949 | Chapman et al. | 502/239 |
| 4,743,575 | 5/1988 | Jaecker | 502/241 |
| 4,794,100 | 12/1988 | Breder, Jr. | 502/238 |
| 4,801,571 | 1/1989 | Montag et al. | 502/236 |

*Primary Examiner*—Carl F. Dees
*Attorney, Agent, or Firm*—Nick C. Kottis; William H. Magidson; Ralph C. Medhurst

[57] ABSTRACT

Catalysts containing a reducible compound on a silica-containing support are provided for the conversion of a lower molecular weight alkane to more valuable, higher molecular weight hydrocarbons.

14 Claims, 1 Drawing Sheet

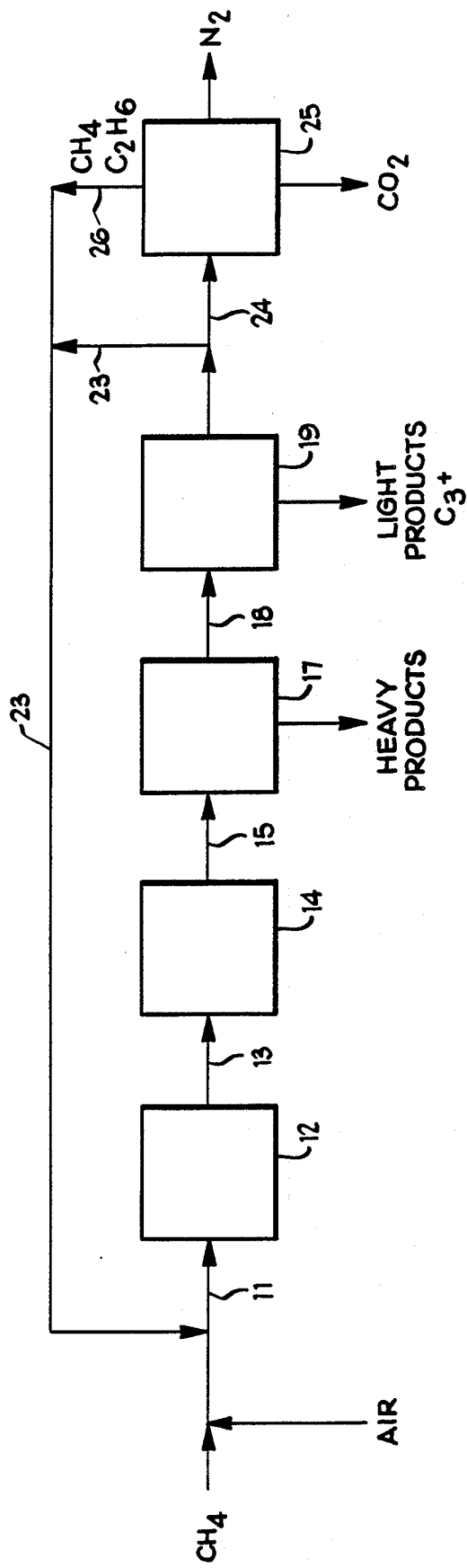

CATALYSTS FOR CONVERSION OF A LOWER ALKANE

This is a continuation, division, of application Ser. No. 706,731, filed Feb. 28, 1985 now U.S. Pat. No. 4,814,539.

BACKGROUND OF THE INVENTION

1. Field of the Invention

This invention relates generally to the conversion of a lower molecular weight alkane to more valuable, heavier hydrocarbons, and more particularly concerns an aforesaid conversion which comprises the oxidative coupling of the alkane and the oxidative coupling catalyst employed therein.

2. Description of the Prior Art

A major source of lower molecular weight alkanes is natural gas. Lower molecular weight alkanes are also present in coal deposits and are formed during numerous mining operations, in various petroleum processes and in the above- or below-ground gasification or liquefaction of coal, tar sands, oil shale and biomass.

It is highly desirable to convert lower molecular weight alkanes to more valuable and higher molecular weight materials and a number of attempts to do so have been reported. For example, G. E. Keller and M. M. Bhasin (J. Catal. 73, 1982, 9–19) have shown that in the presence of catalysts methane can be converted to $C_2$ hydrocarbons, but that the yields of ethylene and ethane are low and amount to only from 10 to 50 percent of the reacted methane. To improve the selectivity for the production of the desired $C_2$ hydrocarbons and to suppress the undesirable further reaction of the $C_2$ hydrocarbons initially formed to produce carbon dioxides, Keller and Bhasin propose a special reaction method: the catalyst is first charged with oxygen by the passage over it of a gas containing oxygen; then in a second step, the oxygen in the gas chamber of the catalytic reactor is replaced by an inert gas; in a third step, methane is fed over the catalyst which partially produces the desired reaction; in a fourth and last step, an inert gas is again led through the reactor to supplant the residual methane and the resulting product, before the sequence of steps is repeated. In this process, depending on the catalyst used and the temperature selected, the selectivities for the production of $C_2$ hydrocarbons range from about 5 to about 45%, and the selectivities for the production of $CO_2$ range from about 55 to 95%, with the conversions of methane ranging between 1 and 10%.

Keller and Bhasin arrive at the conclusion that the oxidative coupling is only highly selective to the higher hydrocarbons when the reaction takes place in the absence of gas-phase oxygen and the oxidative coupling of the hydrocarbons should be caused by reaction with the lattice oxygen of the metal oxides, which are thus reduced by two valency stages. Since the lattice oxygen available in the catalyst is predetermined, for every measured unit of the catalyst only a limited quantity of hydrocarbons can be reacted.

It is evident that the modus operandi in Keller and Bhasin is costly in terms of apparatus as well as being simultaneously linked with small yields in space-time terms and high operating and investment costs. Moreover, the attainable methane conversions and/or the resultant space-time yields are too small for a commercial installation according to the data of the authors. Furthermore, the only products reported are $C_2$ hydrocarbons.

Jones et al., U.S. Pat. Nos. 4,443,664-9 disclose methods for synthesizing hydrocarbons containing as many as 7 carbon atoms from a methane source which comprise contacting methane with a reducible oxide of antimony, germanium, bismuth, lead, indium or manganese. These patents also disclose that the reducible oxides can be supported by a conventional support material such as silica, alumina, titania, and zirconia. Specific supports disclosed are Houdry HSC 534 silica, Cab-O-Sil, Norton alpha-alumina and Davison gamma-alumina. The ranges of reaction temperatures disclosed in the aforesaid patents are from a lower limit of 500° C. to an upper limit of 800° C.–1000° C. In the disclosed processes, the reducible oxide is first reduced and is then regenerated by oxidizing the reduced composition with molecular oxygen, either in a second zone or by alternating the flow of a first gas comprising methane and the flow of an oxygen-containing gas. The highest yield of hydrocarbon products reported was only about 2.1% of the methane feed, when a reducible oxide of manganese was employed.

Furthermore, Baerns, West German patent application No. 3,237,079.2, discloses a method for the production of ethane or ethylene by the reaction of methane and an oxygen-containing gas at a temperature between 500° C. and 900° C, at an oxygen partial pressure of less than about 0.5 atmosphere at the reactor entrance, with a ratio of methane partial pressure-to-oxygen partial pressure greater than 1 at the reactor entrance and in the presence of a solid catalyst free of acidic properties. As disclosed, the method can be performed with or without recycle of remaining unreacted methane. The highest molecular weight product formed in the disclosed method is propane, and the highest collective selectivity for the formation of ethane, ethylene and propane is only about 65% of the methane converted.

Baerns discloses that oxides of the metals of Groups III-VII of the Periodic Table are suitable for use as catalysts in the method disclosed therein and that the oxides of lead, manganese, antimony, tin, bismuth, thallium, cadmium and indium are particularly preferred. Baerns further discloses that the metal oxides can be employed with or without a carrier and that specifically preferred carriers are alumina, silica, silicon carbide and titania. Specific examples of carrier materials disclosed were formed from gamma-alumina having BET surface areas of 160–166 m²/gm, silica having a BET surface area of 290 m²/gm, bismuth oxide, aluminum silicate, and titania.

OBJECTS OF THE INVENTION

It is therefore a general object of the present invention to provide a method for converting a lower molecular weight alkane to more valuable, heavier hydrocarbons which meets the aforementioned requirements and solves the aforementioned problems of prior art methods.

More particularly, it is an object of the present invention to provide a method for converting a lower molecular weight alkane to more valuable, heavier hydrocarbons with a high degree of conversion of the alkane.

It is another object of the present invention to provide a method for converting a lower molecular weight alkane to more valuable, heavier hydrocarbons with a high degree of selectivity for the production of heavier hydrocarbons.

It is a similar object of the present invention to provide a method for converting a lower molecular weight alkane to more valuable, heavier hydrocarbons which affords a high yield of heavier hydrocarbons.

Other objects and advantages of the present invention will become apparent upon reading the following detailed description and appended claims, and upon reference to the accompanying drawing.

SUMMARY OF THE INVENTION

These objects are achieved by an improved oxidative coupling catalyst comprising a reducible compound of lead, antimony, vanadium, tin, bismuth, cadmium,, indium, manganese or thallium or a mixture thereof and a support comprising silica having a surface area less than about 175 $m^2/gm$, wherein the reducible compound is at a level of from about 2 to about 50 weight percent, calculated as the oxide of the reducible metal and based on the weight of the catalyst. The present invention is also an improved method for converting at least one feedstock alkane containing from 1 to 3 carbon atoms to more valuable, higher molecular weight hydrocarbons, comprising contacting the feedstock alkane with an oxygen-containing gas in a reactor in the presence of the aforesaid oxidative coupling catalyst at a temperature in the range of from about 600° C. to about 1000° C.

BRIEF DESCRIPTION OF THE DRAWING

For a more complete understanding of this invention, reference should now be made to the embodiments illustrated in greater detail in the attached drawing and described below by way of examples of the invention. In the drawing, FIG. 1 is a schematic illustration of a preferred embodiment of the method of the present invention in which: (a) a methane feedstock is combined with air in the presence of an oxidation coupling catalyst of this invention and is initially partially converted to a mixture comprising ethane and ethylene; (b) the resulting product stream is subjected to an oligomerization treatment in which the ethylene in the product stream is catalytically aromatized to form heavy and light aromatics; (c) the resulting heavy aromatics formed in the product stream in step (b) are separated from the product mixture; (d) the resulting light aromatics formed in the product stream in step (b) are separated from the product mixture; (e) after separation of a slip stream from the remaining product mixture, the remaining product mixture is recycled to step (a) for additional conversion of remaining unreacted feedstock alkane; and (f) at least a portion of the nitrogen and carbon dioxide components of the slip stream are separated from the slip stream and the remainder of the slip stream is then recycled to step (a) for additional conversion of remaining unreacted feedstock alkane.

It should be understood that the drawing is a schematic illustration, and that in certain instances, details which are not necessary for an understanding of the present invention or which render other details difficult to perceive may have been omitted. It should be understood, of course, that the invention is not necessarily limited to the particular embodiments illustrated herein.

DETAILED DESCRIPTION OF THE DRAWING INCLUDING PREFERRED EMBODIMENTS

Turning first to FIG. 1, there is shown schematically a preferred embodiment of the method of this invention. Methane, illustrative of a feedstock comprising at least one alkane containing from 1 to 3 carbon atoms is mixed with air, as a source of oxygen, and the resulting mixture is introduced through line 11 into a first reactor 12 where it is contacted with a catalyst of the present invention for the oxidative coupling of the aforesaid alkane. The effluent from the first reactor 12 is a gaseous product stream comprising carbon dioxide, nitrogen, any remaining unreacted feedstock alkane and oxygen, and ethane and ethylene, illustrative of alkane and alkene products having higher molecular weights than the feedstock alkane from which they are formed, and is introduced through line 13 into a second reactor 14, where it is contacted with a suitable oligomerization catalyst under aromatization conditions. The effluent from the second reactor 14 comprises carbon dioxide, nitrogen, any remaining unreacted feedstock alkane and oxygen, and higher molecular weight alkane and aromatic products, and is passed through line 15 and a first separator 17 where the separation of any higher boiling products produced in the second reactor 14 is effected. The remaining lower boiling materials are then withdrawn as a gaseous mixture in line 18 from the first separator 17 and introduced into a second separator 19 where lower boiling normally liquid products and optionally at least a portion of the gaseous hydrocarbon products having molecular weights above the feedstock alkane from which they were ultimatley formed are separated. The gaseous effluent from the second separator 19, comprising carbon dioxide, nitrogen and any remaining unreacted feedstock alkane and oxygen, is then split into two streams. The first resulting stream is a major portion of the gaseous effluent from the second separator 19, and is recycled in line 23 as feedstock back to the first reactor 12. The second resulting stream is a minor portion of the gaseous effluent from the second separator 19, has the same composition as the aforesaid first resulting stream, but is passed in line 24 through a third separator 25 where at least a portion of the remaining unreacted feedstock alkane, and ethane is removed therefrom and recycled through line 26 and line 23 as feedstock back to the first reactor 12.

It should be understood that FIG. 1 illustrates merely one preferred embodiment of the method and catalyst of this invention and that the present invention is not limited to the particular embodiment illustrated in FIG. 1.

Generally, a suitable feedstock for the method of this invention comprises at least one of methane, ethane and propane, preferably comprises methane and more preferably comprises a mixture of methane and ethane. Thus, a suitable feedstock for the method of this invention comprises natural gas, gases formed during mining operations, in petroleum processes or in the above- or belowground gasification or liquefaction of coal, tar sands, oil shale and biomass.

The oxygen-containing gas for use in the method of this invention can vary in molecular oxygen content from that of air to oxygen gas itself. Air or enriched air is a preferred source of molecular oxygen. The oxygen-containing gas should provide a gas-vapor effluent mixture from the oxidative coupling reactor containing (measured on a solid-free basis) from about 2 to about 8 volume percent of oxygen, in order to avoid the flammability limits in such mixture.

The oxidative coupling reaction is performed at a temperature in the range of from about 600° C. to about 1000° C., preferably in the range of from about 700° C. to about 850° C. The oxidative coupling step of the method of this invention is performed under a total absolute pressure preferably in the range of from about 1 atmosphere to about 10 atmospheres, and more preferably in the range of from about 1 atmosphere to about 5 atmospheres. The ratio of the combined partial pressures of the feedstock alkanes containing from 1 to 3 carbon atoms in the feedstock-to-the oxygen partial pressure at the entrance of the reactor in the oxidative coupling step is preferably in the range of from about 2:1 to about 40:1 and more preferably in the range of from about 5:1 to about 30:1. The combined partial pressures of the alkanes in the feedstock containing from 1 to 3 carbon atoms at the entrance to the oxidative coupling reactor is preferably in the range of from about 0.1 to about 10 atmospheres, and more preferably in the range from about 0.2 to about 5 atmospheres. The oxygen partial pressure at the entrance to the oxidative coupling reactor is preferably in the range from about 0.01 to about 5 atmospheres and more preferably in the range of from about 0.02 to about 0.7 atmospheres. The oxygen partial pressure in the gaseous effluent from the reactor in the oxidative coupling step is preferably substantially zero.

The oxidative coupling step is performed preferably at a space velocity, calculated for a reaction pressure of one atmosphere absolute, of from about 100 to about 10,000 cubic centimeters of total feed gas comprising feedstock alkane containing from 1 to 3 carbon atoms per hour per cubic centimeter of catalyst and more preferably at a space velocity of from about 500 to about 5000 cubic centimeters of total feed gas comprising feedstock alkane containing from 1 to 3 carbon atoms per hour per cubic centimeter of catalyst. For the purposes of this definition of the space velocity, the feedstock alkane comprises from about 10 volume percent to about 80 volume percent of the total feed gas.

The catalyst of this invention employed in the oxidative coupling step of the method of this invention comprises a reducible compound of lead, antimony, germanium, vanadium, tin, bismuth, cadmium, indium, manganese, thallium, or a mixture thereof Preferably, the reducible compound employed is an oxide, sulfide, sulfate, or carbonate of lead, antimony, germanium, vanadium, tin, bismuth, cadmium, indium, manganese, thallium, or a mixture thereof. The oxidative coupling catalyst more preferably comprises a reducible compound of lead and most preferably comprises a lead oxide. If a reducible compound of lead is present, the presence of additional reducible compounds of other metals, such as zirconium and titanium, which themselves are not effective catalysts, serves to promote the activity of the lead compound in the oxidative coupling reaction.

The oxidative coupling catalyst of this invention additionally comprises a silica support. Preferably, the support of the oxidative coupling catalyst of this invention is silica. Such support has a surface area in the range of from about 1 m$^2$/gm to about 175 m$^2$/gm, and preferably in the range of from about 5 m$^2$/gm to about 75 m$^2$/gm.

The reducible compound component of the oxidative coupling catalyst of this invention comprises preferably from about 2 weight percent to about 50 weight percent of the oxidative coupling catalyst, and more preferably from about 10 weight percent to about 30 weight percent of the oxidative coupling catalyst, calculated as the reducible metal oxide and based on the total weight of the oxidative coupling catalyst.

The oxidative coupling catalyst of this invention can be prepared by impregnation of the aforesaid support with at least one precursor of the reducible metal compound. Any convenient, conventional impregnation technique can be employed for this purpose. For example, a soluble compound of the metal of the reducible metal oxide can be added to a sol or gel of the silica. This composition is then thoroughly blended into the sol or gel mixture, and subsequently co-gelled by the addition of a dilute ammonia solution. The resulting co-gelled material is then dried. In another method of preparation, the silica is gelled, dried, and cooled and the resulting material is then impregnated with one or more solutions of a soluble compound of the metal of the reducible metal oxide.

Preferably, as will be described hereinbelow, the support containing the reducible metal compound or precursor thereof is calcined, regardless of the method of preparation used. In such case, the calcination conditions are preferably calcining at a temperature of from about 500° C. to about 1050° C. for from about 2 hours to about 36 hours and more preferably calcining in air at a temperature of from about 950° C. to about 1050° C. for from about 4 hours to about 20 hours. More preferably, the support is also calcined prior to incorporating the reducible metal compound or its precursor therein. In such case, the catalyst is calcined preferably at a temperature of from about 800° C. to about 1100° C. for from about 2 hours to about 36 hours and more preferably at a temperature of from about 950° C. to about 1050° C. for from about 4 hours to about 16 hours.

It has been found that the selectivity of the oxidative coupling catalyst for the formation of coupled products can be increased by the additional incorporation of an alkali metal component into the support. The presence of the alkali metal component in the oxidative coupling catalyst also permits the concentration of the reducible metal component in the catalyst to be reduced without decreasing the selectivity of the catalyst of the formation of coupled products. Preferably, the metal of the alkali metal component is sodium, potassium or lithium. The alkali metal component is present in the catalyst at a concentration of preferably from about 0.1 to about 6 weight percent, more preferably from about 0.5 to about 3 weight percent, calculated as the alkali metal oxide and based on the weight of the catalyst. A compound of the alkali metal can be deposited by any convenient, conventional technique such as impregnation or spray drying, before, during or after deposition of the metal of the reducible metal component on the catalyst support. Upon calcination, the alkali metal component is converted to the form of its metal oxide.

The gaseous mixture resulting from the oxidative coupling reaction comprises any remaining unreacted feedstock alkane and oxygen and saturated and unsaturated aliphatic hydrocarbon products having higher molecular weights than the feedstock alkane from which they were formed. In addition, if air is employed as the source of molecular oxygen in the oxidative coupling step of the method of the present invention, the effluent from the oxidative coupling step also contains nitrogen and carbon dioxide.

In order to increase the conversion of the feedstock alkane in the oxidative coupling step and the yield of the desired products therefrom, it is desirable to recycle the unconverted feedstock alkane to the oxidative coupling step in a preferred embodiment of the method of this invention. However, recycle of the entire gaseous product mixture from the oxidative coupling reaction to the oxidative coupling step results in a decrease of both the selectivity for the formation of coupled products and the yield of coupled products. Although the presence of saturated coupled products such as ethane in the feed to the oxidative coupling reaction and, hence, in the product mixture recycled to the oxidative coupling reaction affords a surprising increase in the selectivity for both the formation of coupled products and the yield of coupled products in the oxidative coupling step, the presence of unsaturated coupled products such as ethylene and acetylene in the feed to the oxidative coupling reaction and, hence, in the recycled product mixture, has a substantial deleterious effect on the selectivity for the formation of and yield of coupled products in the oxidative coupling step. Thus, in order to increase the conversion of the feedstock alkane and yield of the desired coupled products therefrom, the recycled gaseous mixture must be relatively free of unsaturated coupled products.

Thus, in a preferred embodiment of the method of this invention, prior to being recycled, the gaseous product mixture from the oxidative coupling reaction is contacted with an oligomerization catalyst under aromatization conditions in order to remove unsaturated coupled products therefrom. Surprisingly, the use of certain acidic oligomerization catalysts permits substantially complete removal of the unsaturated hydrocarbons even at atmospheric pressure and from the dilute hydrocarbon streams from the oxidative coupling reaction. The aromatization conditions include a temperature preferably in the range of from about 50° C. to about 500° C. and more preferably in the range of from about 200° C. to about 400° C. The aromatization conditions also include a total absolute pressure preferably in the range of from about 1 atmosphere to about 10 atmospheres and more preferably in the range of from about 1 atmosphere to about 5 atmospheres. The aromatization conditions also include a space velocity, calculated for a reaction pressure of one atmosphere absolute, preferably in the range of from about 100 to about 5,000 cubic centimeters of the gaseous mixture per hour per cubic centimeter of the oligomerization catalyst and more preferably in the range of from about 200 to about 2,000 cubic centimeters of the gaseous mixture per hour per cubic centimeter of the oligomerization catalyst.

The oligomerization catalyst comprises a solid having acidic sites and comprising a molecular sieve, a pillared smectite or vermiculite clay or a combination thereof, or a combination thereof with an amorphous refractory inorganic oxide. Suitable molecular sieves for use in the oligomerization catalyst employed in the method of this invention include a crystalline aluminosilicate, crystalline borosilicate, or de-aluminated crystalline aluminosilicate, or combination thereof. A suitable crystalline aluminosilicate includes natural or synthetic chabazite, clinoptilolite, erionite, mordenite, zeolite A, zeolite L, zeolite X, zeolite Y, ultrastable zeolite Y, zeolite omega, or a ZSM-type zeolite such as ZSM-5, ZSM-11, ZSM-12, ZSM-35, ZSM-38 or ZSM-48.

Mordenite-type crystalline aluminosilicates have been discussed in the patent art, for example, in Kimberlin, U.S. Pat. No. 3,247,098; Benesi et al., U.S. Pat. No. 3,281,483; and Adams et al., U.S. Pat. No. 3,299,153. Synthetic mordenite-type crystalline aluminosilicates, designated as Zeolon, are available from the Norton Company of Worcester, Massachusetts. Another example of a crystalline molecular sieve that is suitable for use in the oligomerization catalyst employed in the method of the present invention is a Y-type zeolitic crystalline aluminosilicate. Y-type, zeolitic molecular sieves are discussed in U.S. Pat. No. 3,130,007.

Ultrastable, large-pore, Y-type, zeolitic crystalline aluminosilicate material is also suitable for use in the oligomerization catalyst in the method of this invention and is described in U.S. Pat. Nos. 3,293,192 and 3,449,070. By large-pore material is meant a material that has pores which are sufficiently large to permit the passage thereinto of benzene molecules and larger molecules and the passage therefrom of reaction products. The ultrastable, large-pore, Y-type, zeolitic crystalline aluminosilicate material that is suitable for use in the oligomerization catalyst employed in the method of this invention exhibits a cubic unit cell dimension and hydroxyl infrared bands that distinguish it from other aluminosilicate materials. The cubic unit cell dimension of the aforesaid ultrastable, large-pore, crystalline aluminosilicate is within the range of about 24.20 Å to about 24.55 Å. The hydroxyl infrared bands obtained with the aforesaid ultrastable, large-pore, crystalline aluminosilicate material are a band near $3,745$ cm$^{-1}$ ($3,745\pm5$ cm$^{-1}$), a band near $3,695$ cm$^{-1}$ ($3,690\pm10$ cm$^{-1}$), and a band near $3,625$ cm$^{-1}$ ($3,610\pm15$ cm$^{-1}$). The band near $3,745$ cm$^{-1}$ may be found on many of the hydrogen-form and de-cationized aluminosilicate materials, but the band near $3,695$ cm$^{-1}$ and the band near $3,625$ cm$^{-1}$ are characteristic of the aforesaid ultrastable, large-pore, Y-type, zeolitic crystalline aluminosilicate material that is used in the catalyst of the present invention. The ultrastable, large-pore, Y-type, zeolitic crystalline aluminosilicate material is also characterized by an alkaline metal content of less than 1%.

Other molecular sieve materials that are useful in the catalyst employed in the method of the present invention are ZSM-type crystalline aluminosilicate molecular sieves. Suitable crystalline aluminosilicates of this type typically have silica-to-alumina mole ratios of at least about 12:1 and pore diameters of at least 5 Å. A specific example of a useful crystalline aluminosilicate zeolite of the ZSM-type is ZSM-5, which is described in detail in U.S. Pat. No. 3,702,886. Other crystalline aluminosilicate zeolites of the ZSM-type contemplated according to the invention include ZSM-11, which is described in detail in U.S. Pat. No. 3,709,979; ZSM-12, which is described in detail in U.S. Pat. No. 3,832,449; ZSM-35, which is described in U.S. Pat. No. 4,016,245; and ZSM-38, which is described in detail in U.S. Pat. No. 4,046,859. A preferred crystalline aluminosilicate zeolite of the ZSM-type is ZSM-5.

Dealuminated crystalline aluminosilicate zeolites having higher silica-to-alumina mole ratios than in those formed by available synthesis of crystalline aluminosilicate zeolites are also suitable for use in the oligomerization catalyst of the method of the present invention and can be produced by the removal of aluminum from the structural framework of the crystalline aluminosilicate zeolite by appropriate chemical agents. A considerable amount of work on the preparation of aluminum deficient faujasites has been performed and is reviewed in Advances in Chemistry, Series No. 121, "Molecular Sieves," G. T. Kerr, American Chemical Society, 1973. Specific methods for preparing dealuminized zeolites are described in the following, and reference is made to them for details of the method: Catalysis by Zeolites (International Symposium on Zeolites, Lyon, September 9-11, 1980), Elsevier Scientific Publishing Co., Amsterdam, 1980 (dealuminization of zeolite Y with silicon tetrachloride); U.S. Pat. No. 3,442,795 and British Patent No. 1,058,188 (hydrolysis and removal of aluminum by chelation); British Pat. No. 1,061,847 (acid extraction of aluminum); U.S. Pat. No. 3,493,519 (aluminum removal by steaming and chelation); U.S. Pat. No. 3,591,488 (aluminum removal by steaming); U.S. Pat. No. 4,273,753 (dealuminization by silicon halides and oxyhalides); U.S. Pat. No. 3,691,099 (aluminum extraction with acid); U.S. Pat. No. 4,093,560 (dealuminization by treatment with salts); U.S. Pat. No. 3,937,791 (aluminum removal with Cr(III) solutions); U.S. Pat. No. 3,506,400 (steaming followed by chelation); U.S. Pat. No. 3,640,681 (extraction of aluminum with acetylacetonate followed by dehydroxylation); U.S. Pat. No. 3,836,561 (removal of aluminum with acid); DE-OS 2,510,740 (treatment of zeolite with chlorine or chlorine-contrary gases at high temperatures), Dutch Patent No. 7,604,264 (acid extraction), Japanese No. 53,101,003 (treatment with EDTA or other materials to remove aluminum) and J. Catalysis, 54, 295 (1978) (hydrothermal treatment followed by acid extraction).

An additional molecular sieve that can be used in the oligomerization catalyst of the present invention is a crystalline borosilicate, which is described in Klotz, U.S. Pat. No. 4,269,813, which patent is specifically incorporated herein by reference. A suitable crystalline borosilicate is a molecular sieve material having the following composition in terms of mole ratios of oxides:

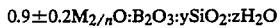

$0.9 \pm 0.2 M_{2/n}O:B_2O_3:ySiO_2:zH_2O$ wherein M is at least one cation having a valence of n, y is within the range of 4 to about 600, and z is within the range of 0 to about 160, and providing an X-ray pattern providing the following X-ray diffraction lines and assigned strengths:

| d, Angstroms | Assigned Strength |
|---|---|
| 11.2 ± 0.2 | W-VS |
| 10.0 ± 0.2 | W-MS |
| 5.97 ± 0.07 | W-M |
| 3.82 ± 0.05 | VS |
| 3.70 ± 0.05 | MS |
| 3.62 ± 0.05 | M-MS |
| 2.97 ± 0.02 | W-M |
| 1.99 ± 0.02 | VW-M |

Suitable methods for preparing the aforesaid crystalline borosilicate molecular sieve are disclosed in Klotz, U.S. Pat. No. 4,269,813 and in Haddid, European patent application No. 82303246.1 which was published on Jan. 5, 1983.

Pillared smectite and vermiculite clays, which are also suitable for use in, or as, the oligomerization catalyst employed in the method of this invention, are often referred to in the literature as pillared interlayered clays and occasionally as molecular sieves. The smectite clays comprise montmorillonite, beidellite, montronite, volchonskoite, hectorite, saponite, stevensite, sauconite and pimelite. Some pillared smectite and vermiculite clay materials that are suitable for use in the support of the catalyst employed in the method of this invention, and methods for preparing such clays, are disclosed in Vaughan et al., U.S. Pat. No. 4,176,090; Shabria et al., U.S. Pat. No. 4,216,188; Shabtai, U.S. Pat. No. 4,238,364; D'Aniello, U.S. Pat. No. 4,380,510; Pinnavaia, "Intercalated Clay Catalysts," Science, Vol. 220, pages 365–371 (Apr. 22, 1983) and Vaughan et al., "Preparation of Molecular Sieves Based on Pillared Interlayered Clays (PILC)," Fifth International Conference on Zeolites, pages 94–101 and in the references cited therein. Preferably, a suitable pillared smectite or vermiculite clay comprises a multiplicity of cations interposed between the molecular layers of the clay and maintaining the spacing between the molecular layers in the range of from about 6 Å to about 10 Å at a temperature of at least 300° C. in an air atmosphere for at least 2 hours.

Preferably, when the oligomerization catalyst comprises an aforesaid molecular sieve material or an aforesaid pillared smectite or vermiculite clay material or a combination thereof, the oligomerization catalyst also comprises a porous amorphous refractory inorganic oxide comprising an oxide of an element from Groups IIA, IIIA, IIIB, IVA or IVB of the Periodic Table. In such cases, the concentrations of the amorphous inorganic oxide and of the molecular sieve material and/or pillared smectite or vermiculite clay material are not critical. Preferably, the amorphous refractory inorganic oxide content is at least high enough to give the oligomerization catalyst sufficient strength and integrity so that it can be employed in the method of the present invention without appreciable damage to the catalyst. In such case, the total concentration of the molecular sieve material and/or pillared smectite or vermiculite clay material in such mixture is preferably from about 5 to about 95 weight percent, and the total concentration of the amorphous refractory inorganic oxide in the mixture is preferably from about 5 to about 95 weight percent, based on the weight of the support.

Preferably, when the oligomerization catalyst comprises a mixture of a molecular sieve and/or pillared smectite or vermiculite clay and an amorphous refractory inorganic oxide, the oligomerization catalyst is in the form of a dispersion of the molecular sieve component and/or pillared smectite or vermiculite clay component in a matrix of the amorphous refractory inorganic oxide. Such dispersions can be prepared by well-known techniques, such as blending the molecular sieve component and/or pillared smectite or vermiculite clay component, preferably in finely-divided form, into a sol, hydrosol or hydrogel of the amorphous refractory inorganic oxide, and then adding a gelling medium, such as ammonium hydroxide, and stirring to produce a gel. Alternately, the molecular sieve component and/or pillared smectite or vermiculite clay component is blended into a slurry of the amorphous inorganic oxide. In either case, the resulting mixture can be dried, shaped, if desired, and then calcined to form the final support component. A less preferred, but still suitable, method for preparing a suitable dispersion of the molecular sieve component and/or pillared smectite or vermiculite clay component in the amorphous refractory inorganic oxide is to dry-blend particles of each, preferably in finely-divided form, and then to conduct any desired shaping operations, such as pelletizing or extrusion; the resulting mixture is then calcined.

The oligomerization catalyst employed in the method of this invention comprises a solid having acidic sites. Consequently, it is highly preferred that the aforesaid molecular sieve or pillared clay materials containing exchangeable cations and employed in the oligomerization catalyst are in their proton-exchanged forms. The proton forms of these materials are particularly effective at the low pressures employed in the oligomerization step of the method of this invention.

The aforesaid molecular sieve and pillared clay materials could also be in their metal-exchanged or metal-impregnated forms, provided that such metal-containing materials still have acidic properties. In such case, the metal employed should be one, such as zinc, which promotes the oligomerization-aromatization activity of the catalyst. Any convenient, conventional cation-exchange or cation-impregnation technique can be employed for this purpose.

Suitable conditions for drying the above-described supports comprise a temperature in the range of from about 90° C. to about 200° C. and a drying time of from about 0.5 to about 30 hours. Suitable calcination conditions in such methods comprise a temperature in the range of about 480° C. to about 760° C. and a calcination time of from about 2 to about 5 hours. Preferred drying and calcination conditions are a temperature of about 120° C. for about 1-2 hours and a temperature of about 538° C. for about 1-2 hours, respectively.

The gaseous mixture resulting from the oligomerization reaction comprises any remaining unreacted feedstock alkane and oxygen and a heavy aromatics product, a light aromatics product and at least one higher molecular weight saturated aliphatic hydrocarbon product. Prior to recycling the unreacted feedstock alkane component of this mixture to the oxidative coupling step, the desired hydrocarbon products are separated from it. This can be effected using any convenient, conventional method. One suitable method to accomplish this separation involves first separating the higher boiling, liquefiable products such as alkylbenzenes and alkylnaphthalenes by scrubbing the gaseous mixture in a suitable solvent at a sufficiently low temperature, such as a cooled oil scrubber, such that the aforesaid liquifiable products are selectively dissolved in it. The resulting liquefied products are recovered from the oil scrubber, for example, by distillation of the scrubbing oil. The remaining gaseous components of the product stream comprise remaining unreacted feedstock alkane and oxygen and lower boiling products, such as lighter aromatics and saturated aliphatics, and pass through the oil scrubber as a gaseous mixture.

The lower boiling products are next separated from this mixture by any convenient, conventional technique. One highly effective, novel technique involves passing the mixture through a charcoal bed. The unreacted feedstock alkane and oxygen pass through the charcoal bed faster than do the products and are recycled to the oxidative coupling step before the products saturate and emerge from the bed. When the bed becomes saturated with the products, the products begin to emerge from the bed, and the bed is removed from service and replaced in service by a fresh charcoal bed. The lower boiling products are then removed from the saturated bed and collected. This separation step can be performed either by removing the bed from service when the lowest boiling product, for example, ethane, begins to emerge from the bed or, as illustrated in FIG.1, by removing the bed from service when higher boiling (but still low boiling products, for example, C3+hydrocarbons, begin to emerge from the bed.

The adsorption or saturation step is conducted at a lower temperature than the desorption or product-removal step. The gases enter the charcoal bed at a temperature, for example, below about 65° C. and at substantially atmospheric pressure. Under these conditions as much as 20-30 percent of the weight of the bed is covered by adsorbed product. When the bed can hold no more hydrocarbon as shown by the presence of higher hydrocarbons in the effluent gas from the charcoal bed, the feed gas is stopped and superheated steam is passed into the bed. As the bed heats up, it desorbs hydrocarbons which pass out of the bed with excess steam and are condensed out in a separate operation. When the bed has been heated to some temperature preferably in the range of 105-300° C. and desorption of hydrocarbons has diminished substantially, the charcoal bed is cooled down and then returned to service. Any oleophilic charcoal works well as do certain hydrophobic clays. In particular, coconut and bituminous charcoal have been shown to be both highly effective and inexpensive.

When the oxygen-containing gas comprises air, the gaseous mixture which remains after the step of recovering the lower boiling products comprises nitrogen and carbon dioxide in addition to remaining unreacted feedstock alkane and oxygen. Thus, nitrogen and carbon dioxide would build up in the recycled portion of the feed to the oxidative coupling step. This buildup of nitrogen and carbon dioxide in the recycle to the oxidative step can be eliminated conveniently by separating a slip stream from the recycle gas and venting a small portion, for example, 10 percent, of the recycle gas before the recycle gas is returned to the oxidative coupling step. However, in addition to nitrogen and carbon dioxide, the gas vented also contains some unreacted feedstock alkane. In order to maximize the conversion of the feedstock alkane to coupled products, it is desirable to separate the unreacted feedstock alkane component from the slip stream before it is vented and recycle the separated feedstock alkane to the oxidative coupling step. This separation can be effected by any convenient, conventional technique. One highly effective, novel technique involves passing the slip stream through a second charcoal bed. The nitrogen passes through the charcoal bed faster than does the unreacted feedstock alkane and is vented before the unreacted feedstock alkane saturates and emerges from the bed. When the bed becomes saturated with feedstock alkane, the feedstock alkane begins to emerge from the bed, and the bed is removed from service and replaced in service by a fresh charcoal bed. The feedstock alkane is then removed from the saturated bed and recycled to the oxidative coupling step.

For reclaiming feedstock alkane from the slip stream, a somewhat different mode of operating the charcoal bed is more advantageous than that described hereinabove. In this case, because of the low adsorptive capacity that charcoals have for methane, it is desirable to use rapid adsorption-desorption cycles, without externally changing the temperature of the bed. It has been advantageous when such beds become saturated with methane, ethane and carbon dioxide (the nitrogen having been discharged) at a temperature up to 65° C. and substantially atmospheric pressure absolute, to remove adsorbed methane by evacuating the bed. With progressive evacuation down to about 28-29 inches of mercury vacuum, methane, carbon dioxide, and ethane are removed separately and sequentially, thus permitting an effective separation of such components. Methane and, if desired, higher hydrocarbons are returned to the recycle system; while carbon dioxide is selectively rejected.

The present invention will be more clearly understood from the following specific examples.

EXAMPLES 1-149

Examples 1-149 demonstrate significant parameters of the oxidative coupling catalyst of this invention and of the oxidative coupling reaction of the method of this invention. In each of Examples 1-149, a stream of methane and air was passed through a heated quartz tube (except Examples 28-31 where a ceramic reactor was used) having an inside diameter of 1.43 centimeters and a length of from 10 to 43 centimeters and, in all cases except Examples 1-4 and 28-31, whose internal volume in the middle of the tube was filled with solid particles or pellets. The reaction pressure was approximately one atmosphere absolute. The product gas effluent from the tube was cooled with an ice bath condenser and analyzed. The experimental parameters employed in Examples 1-149 and the results therefrom are presented in Tables 1-19. In all cases except Examples 1-4 and 28-31, the units of space velocity are the volume (in cubic centimeters) of the combination of methane and air fed to the reactor per hour per cubic centimeter of catalyst in the tube. In Examples 1-4 and 28-31, the space velocity is the volume (in cubic centimeters) of the combination of methane and air fed to the reactor per hour per the inside volume (in cubic centimeters) of the reactor. Each of the product selectivity, selectivity for the formation of coupled products ($C_2+$) and yield of $C_2+$ (the product of methane conversion multiplied by the selectivity for the formation of $C_2+$ divided by 100) is reported as mole percent of the carbon in methane in the feed that is converted. $C_4+$ in the tables refers to gaseous products containing at least 4 carbon atoms.

In Examples 1-4, the quartz tube was empty, and very little oxygen was consumed even at the highest reaction temperature, leading to little consumption of methane. However, the selectivity for the formation of coupled products ($C_2+$), based on the amount of methane consumed, was substantial even though most oxides of carbon appeared as carbon monoxide.

In Examples 5-10, when the tube was filled with pellets of Calsicat D (a product of Mallinckrodt, Inc. of Erie, Pa.), a preferred silica support for the preferred oxidative coupling catalyst, when a reaction temperature of at least 850° C. was employed, nearly all oxygen was consumed, and product selectivity for the formation of coupled product was moderate at 53%. The conversion to coupled products increased as the reaction temperature was increased, with ethylene predominating as the coupled product. The selectivity for the formation of coupled products also increased at a given reaction temperature as the $CH_4/O_2$ mole ratio increased.

When ceramic alumina chips were employed as the tube packing, as indicated in Table 3 for Examples 11-13, oxygen consumption was less, but selectivity for the formation of coupled products ($C_2+$) was appreciably better (67-88%) than when Calsicat D was employed as the tube packing. However, high temperatures of the order of 890-945° C. were required to increase oxygen consumption, at which temperatures methane reforming, as evidenced by CO formation, increased substantially.

TABLE 1

| Example | 1 | 2 | 3 | 4 |
|---|---|---|---|---|
| Tube Packing | \multicolumn{4}{c}{Empty Tube} | | | |
| Reactor Temp. (°C.) | 700 | 800 | 850 | 900 |
| Space Velocity | 480 | 480 | 480 | 480 |

TABLE 1-continued

| Example | 1 | 2 | 3 | 4 |
|---|---|---|---|---|
| Tube Packing | | Empty Tube | | |
| $CH_4/O_2$ (mole ratio) | 9.7/1 | 9.7/1 | 9.7/1 | 9.7/1 |
| $O_2$ Conversion (mole %) | 0.2 | 4 | 12 | 29 |
| $CH_4$ Conversion (mole %) | — | 0.4 | 1.7 | 4.5 |
| Product Selectivity | | | | |
| CO | 0 | 24 | 34 | 41 |
| $CO_2$ | 0 | 0 | 0 | 3 |
| $C_2H_4$ | 0 | 32 | 35 | 39 |
| $C_2H_6$ | 100 | 44 | 31 | 16 |
| $C_2H_2$ | — | — | — | — |
| $C_3$'s | — | — | — | — |
| $C_4$'s+ | — | — | — | — |
| Selectivity to $C_2+$ | 100 | 76 | 66 | 55 |
| Yield of $C_2+$ | nil | 0.3 | 1.1 | 2.5 |

TABLE 2

| Example | 5 | 6 | 7 | 8 | 9 | 10 |
|---|---|---|---|---|---|---|
| Tube Packing | | | Calsicat D Silica | | | |
| Reactor Temp. (°C.) | 700 | 800 | 850 | 900 | 900 | 800 |
| Space Velocity | 1200 | 1200 | 1200 | 1200 | 1000 | 1000 |
| $CH_4/O_2$ (mole ratio) | 9.6/1 | 9.6/1 | 9.6/1 | 9.6/1 | 27/1 | 27/1 |
| $O_2$ Conversion (mole %) | 4.6 | 49 | 94 | 98+ | 97+ | 97+ |
| $CH_4$ Conversion (mole %) | 0.1 | 4.7 | 10 | 12 | 5.5 | 4.1 |
| Product Selectivity | | | | | | |
| CO | 78 | 44 | 25 | 22 | 19 | 35 |
| $CO_2$ | 20 | 20 | 23 | 22 | 15 | 19 |
| $C_2H_4$ | 0 | 16 | 37 | 51 | 62 | 25 |
| $C_2H_6$ | 2 | 20 | 16 | 5 | 4 | 22 |
| $C_2H_2$ | — | — | — | — | — | — |
| $C_3$'s | — | — | — | — | — | — |
| $C_4$'s+ | — | — | — | — | — | — |
| Selectivity to $C_2+$ | 2 | 36 | 53 | 56 | 66 | 47 |
| Yield of $C_2+$ | nil | 1.7 | 5.3 | 6.7 | 3.6 | 1.9 |

TABLE 3

| Example | 11 | 12 | 13 |
|---|---|---|---|
| Tube Packing | | Ceramic Chips | |
| Reactor Temp. (°C.) | 851 | 889 | 945 |
| Space Velocity | 1696 | 1696 | 1696 |
| $CH_4/O_2$ (mole ratio) | 24/1 | 24/1 | 24/1 |
| $O_2$ Conversion (mole %) | 14.3 | 4.1 | 57 |
| $CH_4$ Conversion (mole %) | 0.4 | 0.6 | 3.9 |
| Product Selectivity | | | |
| CO | — | 3 | 26 |
| $CO_2$ | 29 | 9 | 7 |
| $C_2H_4$ | 10 | 27 | 25 |
| $C_2H_6$ | 60 | 58 | 37 |
| $C_2H_2$ | — | — | — |
| $C_3$'s | — | — | — |
| $C_4$'s+ | — | — | — |
| Selectivity to $C_2+$ | 71 | 88 | 67 |
| Yield of $C_2+$ | 0.3 | 0.5 | 2.6 |

A tube packing of 1 percent by weight of potassium bromide on Calsicat D silica (the silica was dispersed in an aqueous solution of potassium bromide; the solution was evaporated; and the silica was then dried and calcined) was employed in Examples 14-17 (Table 4) and was approximately as active and selective as Calsicat D alone. Celite 408, a diatomaceous silica and a product of Johns Manville Company, was employed as the tube packing in Examples 18-21 (Table 5) and afforded relatively poor selectivity. Zirconia containing 2 percent by weight of alumina was employed as the tube packing in Examples 22-25 (Table 6) and promoted only formation of carbon oxides. Alpha Alumina was employed as the tube packing in Example 26 (Table 6) and afforded good activity but relatively low selectivity. Mordenite (Norton Zeolon 100) was employed as the tube packing in Example 27 (Table 7) and formed little coupled product but afforded copious coking. A ceramic α-alumina tube, not containing any tube packing, was employed in Examples 28-31 (Table 7) and was somewhat active at low space velocity and high reaction temperatures and afforded high selectivities for the formation of $C_2$ and $C_3$ products. Magnesium aluminum borate, a mixed oxide, was employed as the tube packing in Examples 32-35 (Table 8) and was only moderately active and afforded only moderate selectivity for the formation of coupled products.

In Examples 36-49, several forms of tube packings of lead oxide on various supports were employed. In Examples 36-38 (Table 9), lead oxide on α-alumina having a surface area of 31 m²/g was highly active in catalyzing the conversion of oxygen even at relatively low reaction temperatures, but with relatively poor selectivities of 44-55%.- for the production of coupled products. By contrast, a low surface area silica (Examples 39-40) was highly selective.

TABLE 4

| Example | 14 | 15 | 16 | 17 |
|---|---|---|---|---|
| Tube Packing | | 1% KBr/Calsicat D Silica | | |
| Reactor Temp. (°C.) | 700 | 800 | 850 | 900 |
| Space Velocity | 1200 | 1200 | 1200 | 1200 |
| $CH_4/O_2$ (mole ratio) | 10/1 | 10/1 | 10/1 | 10/1 |
| $O_2$ Conversion (mole %) | 81 | 98+ | 98+ | 98+ |
| $CH_4$ Conversion (mole %) | 6.9 | 13 | 14 | 16 |
| Product Selectivity | | | | |
| CO | 67 | 34 | 24 | 20 |
| $CO_2$ | 18 | 16 | 22 | 21 |
| $C_2H_4$ | 7 | 34 | 38 | 48 |
| $C_2H_6$ | 9 | 15 | 13 | 6 |
| $C_2H_2$ | 0 | 0 | 0 | 0 |
| $C_3$'s | 0 | 2 | 3 | 4 |
| $C_4$'s | — | — | — | — |
| Selectivity to $C_2+$ | 16 | 51 | 54 | 58 |
| Yield of $C_2+$ | 1.1 | 6.6 | 7.6 | 9.3 |

TABLE 5

| Example | 18 | 19 | 20 | 21 |
|---|---|---|---|---|
| Tube Packing | | Celite 408 | | |
| Reactor Temp. (°C.) | 700 | 800 | 850 | 900 |
| Space Velocity | 1200 | 1200 | 1200 | 1200 |
| $CH_4/O_2$ (mole ratio) | 10/1 | 10/1 | 10/1 | 10/1 |
| $O_2$ Conversion (mole %) | 42 | 97+ | 98+ | 98+ |
| $CH_4$ Conversion (mole %) | 3.2 | 6.8 | 7.2 | 8.0 |
| Product Selectivity | | | | |
| CO | 53 | 61 | 64 | 63 |
| $CO_2$ | 35 | 31 | 26 | 23 |
| $C_2H_4$ | 0 | 3 | 5 | 10 |
| $C_2H_6$ | 13 | 5 | 5 | 4 |
| $C_2H_2$ | 0 | 0 | 0 | 0 |
| $C_3$'s | 0 | 0 | 0 | 0 |
| $C_4$'s | — | — | — | — |
| Selectivity to $C_2+$ | 13 | 8 | 10 | 14 |
| Yield of $C_2+$ | 0.4 | 0.5 | 0.7 | 1.1 |

TABLE 6

| Example | 22 | 23 | 24 | 25 | 26 |
|---|---|---|---|---|---|
| Tube Packing | | $ZrO_2$ + 2% $Al_2O_3$ | | | α-Alumina |
| Reactor Temp. (°C.) | 700 | 800 | 850 | 850 | 800 |
| Space Velocity | 4800 | 4800 | 4800 | 1200 | 8700 |
| $CH_4/O_2$ (mole ratio) | 2/1 | 2/1 | 2/1 | 10/1 | 19.5/1 |
| $O_2$ Conversion (mole %) | 100 | 100 | 100 | 100 | 100 |
| $CH_4$ Conversion (mole %) | 26 | 28 | 33 | 11 | — |
| Product Selectivity | | | | | |
| CO | 20 | 28 | 35 | 64 | 50.4 |
| $CO_2$ | 81 | 72 | 65 | 36 | 34.5 |
| $C_2H_4$ | 0 | 0 | 0 | 0 | 7.2 |
| $C_2H_6$ | 0 | 0 | 0 | 0 | 15.6 |
| $C_2H_2$ | 0 | 0 | 0 | 0 | — |
| $C_3$'s | 0 | 0 | 0 | 0 | 0.6 |
| $C_4$'s | — | — | — | — | — |
| Selectivity to $C_2+$ | 0 | 0 | 0 | 0 | 23 |
| Yield of $C_2+$ | 0 | 0 | 0 | 0 | — |

TABLE 7

| Example | 27 | 28 | 29 | 30 | 31 |
|---|---|---|---|---|---|
| Tube Packing | Mordenite | | Empty Ceramic Reactor | | |
| Reactor Temp. (°C.) | 833 | 840 | 885 | 937 | 915 |
| Space Velocity | 8700 | 1696 | 1696 | 1696 | 848 |
| $CH_4/O_2$ (mole ratio) | 20/1 | 24.1/1 | 24.1/1 | 24.1/1 | 29.1/1 |
| $O_2$ Conversion (mole %) | 92.5 | 3.8 | 7.4 | 19.7 | 43.2 |
| $CH_4$ Conversion (mole %) | 4.4 | nil | 0.5 | 1.8 | 4.1 |
| Product Selectivity | | | | | |
| CO | 51.9 | — | — | 19.3 | 22.7 |
| $CO_2$ | 43.9 | — | — | — | 0.6 |
| $C_2H_4$ | — | 92.2 | 20.4 | 33.6 | 29.1 |
| $C_2H_6$ | 4.2 | — | 64.8 | 33.9 | 35.6 |
| $C_2H_2$ | — | — | — | — | — |
| $C_3$'s | — | 7.8 | 14.8 | 11.8 | 8.3 |
| $C_4$'s+ | — | — | — | 1.4 | 3.7 |
| Selectivity to $C_2+$ | 4.2 | 100 | 100 | 80.7 | 76.7 |
| Yield of $C_2+$ | 0.18 | nil | 0.5 | 1.5 | 3.1 |

TABLE 8

| Example | 32 | 33 | 34 | 35 |
|---|---|---|---|---|
| Tube Packing | | Magnesium Aluminum Borate | | |
| Reactor Temp. °C. | 811 | 851 | 846 | 845 |
| Space Velocity | 1695 | 1695 | 848 | 424 |
| $CH_4/O_2$ (mole ratio) | 22.6/1 | 22.6/1 | 24.9/1 | 30.1/1 |
| $O_2$ Conversion (mole %) | 39.9 | 38.0 | 63.4 | 98.0 |
| $CH_4$ Conversion (mole %) | 2.2 | 3.2 | 3.8 | 3.4 |
| Product Selectivity | | | | |
| CO | 46.7 | 48.7 | 40.2 | 49.1 |
| $CO_2$ | 12.4 | 5.4 | 7.6 | 8.0 |
| $C_2H_4$ | 6.0 | 10.5 | 19.3 | 22.3 |
| $C_2H_6$ | 28.6 | 28.2 | 25.3 | 15.6 |
| $C_2H_2$ | — | 4.6 | 3.5 | 1.7 |
| $C_3$'s | 2.2 | 1.6 | 3.2 | 2.8 |
| $C_4$'s+ | 4.2 | 1.0 | 1.0 | 0.4 |
| Selectivity to $C_2+$ | 41.0 | 45.9 | 52.3 | 42.8 |
| Yield of $C_2+$ | 0.9 | 1.5 | 2.0 | 1.5 |

TABLE 9

| | 36 | 37 | 38 | 39 | 40 |
|---|---|---|---|---|---|
| | | | 20% PbO on | | |
| Example Tube Packing | | α-Alumina | | Calsicat D Silica (24 m²/g) | |
| Reactor Temp. (°C.) | 757 | 818 | 803 | 733 | 830 |

TABLE 9-continued

| Space Velocity | 8700 | 8700 | 8700 | 6600 | 6600 |
|---|---|---|---|---|---|
| $CH_4/O_2$ (mole ratio) | 20/1 | 19/1 | 5.1/1 | 20/1 | 20/1 |
| $O_2$ Conversion (mole %) | 100 | 100 | 100 | 37.9 | 44.1 |
| Product Selectivity | | | | | |
| CO | — | 1.2 | — | — | — |
| $CO_2$ | 48.0 | 44.2 | 55.6 | 37.4 | 9.7 |
| $C_2H_4$ | 17.6 | 26.0 | 21.8 | 2.0 | 20.5 |
| $C_2H_6$ | 32.8 | 26.2 | 20.8 | 60.4 | 68.0 |
| $C_2H_2$ | — | — | — | — | — |
| $C_3$'s | 1.5 | 2.4 | 1.8 | 0.2 | 1.8 |
| $C_4$'s | — | — | — | — | — |
| Selectivity to $C_2+$ | 51.9 | 54.6 | 44.4 | 62.6 | 90.3 |

| Example | 41 | 42 | 43 | 44 | 45 | 46 |
|---|---|---|---|---|---|---|
| Tube Packing | | | 20% PbO on Calsicat D Silica (24 m²/g) | | | |
| Reactor Temp. (°C.) | 835 | 852 | 872 | 896 | 915 | 914 |
| Space Velocity | 3300 | 3300 | 6600 | 3300 | 1320 | 1320 |
| $CH_4/O_2$ (mole ratio) | 21/1 | 21/1 | 19/1 | 20/1 | 10.3/1 | 5.2/1 |
| $O_2$ Conversion (mole %) | 76.8 | 88.0 | 65.8 | 92.3 | 100 | 88.7 |
| $CH_4$ Conversion (mole %) | — | — | 6.8 | 8.5 | 13.4 | 18.7 |
| Product Selectivity | | | | | | |
| CO | — | — | — | — | — | 6.6 |
| $CO_2$ | 9.8 | 9.7 | 8.5 | 9.6 | 14.2 | 18.3 |
| $C_2H_4$ | 31.4 | 35.8 | 30.8 | 37.4 | 43.6 | 30.2 |
| $C_2H_6$ | 57.0 | 52.2 | 53.2 | 42.4 | 26.2 | 20.2 |
| $C_2H_2$ | — | — | 2.7 | 2.8 | 2.0 | 0.0 |
| $C_3$'s | 1.8 | 2.4 | 4.8 | 7.5 | 7.2 | 19.5 |
| $C_4$'7 | — | — | — | 0.4 | 6.8 | 5.6 |
| Selectivity to $C_2+$ | 90.2 | 90.4 | 91.5 | 90.5 | 85.8 | 75.5 |
| Yield of $C_2+$ | | | 6 | 8 | 11 | 14 |

| Example | 47 | 48 | 49 |
|---|---|---|---|
| Tube Packing | | 17% PbO on High Surface Area Silica (245 m²/g) | |
| Reactor Temp. (°C.) | 740 | 740 | 740 |
| Space Velocity | 13,040 | 6135 | 1341 |
| $CH_4/O_2$ (mole ratio) | 10/1 | 10/1 | 10/1 |
| $O_2$ Conversion (mole %) | 19.9 | 26.1 | 53.0 |
| Product Selectivity | | | |
| CO | — | — | 1.6 |
| $CO_2$ | 48.5 | 41.4 | 39.4 |
| $C_2H_4$ | 6.9 | 8.2 | 16.3 |
| $C_2H_6$ | 44.3 | 50.2 | 42.0 |
| $C_2H_2$ | — | — | — |
| $C_3$'s | 0.3 | 0.2 | 0.6 |
| $C_4$'s | — | — | — |
| Selectivity to $C_2+$ | 51.5 | 58.6 | 58.9 |

Examples 39-49 (Table 9) demonstrate the surprising influence on the oxidative coupling reaction of the physical properties of the support employed in the lead oxide catalyst. By contrast to the relatively high surface area supports employed in Examples 47-49, lead oxide on Calsicat D, a low surface area silica, afforded very high conversion of oxygen in all cases, with selectivities for the formation of coupled products in excess of 90% at $CH_4/O_2$ mole ratios of at least 19/1. Furthermore, in such examples, the selectivities for the formation of coupled products were maintained at levels of greater than 75% even at the $CH_4/O_2$ ratio of 5/1. The high surface area silica tube packing employed in Examples 47-49 afforded selectivities for the formation of coupled products that were comparable to those for the α-alumina packing employed in Examples 36-38.

To establish the influence of the surface area of the support used in preparing the oxidative coupling catalyst and of the conditioners under which such support is calcined prior to impregnation, several samples of a high surface area silica (Philadelphia Quartz PQ-CK107G $SiO_2$) with a surface area of 239 m²/gm were calcined under various conditions (indicated in Table 10), converted to catalysts, each containing 20% by weight of PbO, by precipitation of a lead compound from an aqueous solution of its nitrate in the presence of the silica and further calcination in air at about 600° C. to form the PbO-impregnated silica, and then evaluated as catalysts in the oxidative coupling reaction in Examples 50-54. In each evaluation, the following conditions were employed: a reaction temperature of 750-850° C., a space velocity of 6600 cc/hr/cc, and a $CH_4/O_2$ mole ratio of 20. The experimental parameters and results presented in Table 10 for Examples 50-54 illustrate that, as the surface area of the silica is decreased, until the surface area fell to about 21 m²/gm, there was a progressive increase in the selectivity for the production of coupled products.

TABLE 10

| Example | Conditions of Calcination Before Impregnation | Surface Area (m²/gm) | Selectivity to $C_2+$ |
|---|---|---|---|
| 50 | 2 hrs. at 650° C. | 239 | 45 |
| 51 | 8 hrs. at 830° C. | 179 | 66 |
| 52 | 8 hrs. at 920° C. | 116 | 85 |
| 53 | 8 hrs. at 970° C. | 21 | Low Activity |
| 54 | 4 hrs. at 1000° C. | <2 | Inactive |

The catalyst prepared in Example 52 was evaluated in Examples 55-59 as a catalyst for the oxidative coupling reaction under varying conditions of reaction temperature and space velocity. As indicated by the experimental parameters and results presented for Examples 55-59 in Table 11, the degree of oxygen conversion increased as the reaction temperature was increased at a constant space velocity and as the space velocity was decreased.

To establish the influence of the presence in the catalyst of agents, such as alkali metal components which modify the characteristics of the catalyst, such as the acidity of the support, several samples of a low surface area silica (Type 16753 manufactured by Norton Company) having a surface area of 29 cm²/gm were calcined at 550-600° C. with air for 2-3 hours, converted to catalysts, each containing 20% PbO by weight and either no or various amounts of a sodium or magnesium component incorporated thereinto by precipitation of a lead compound and either a sodium or magnesium compound from a solution of their nitrates in an aqueous slurry of the silica and calcination in air to form the PbO- and either $Na_2O$- or MgO-impregnated silica. These metal-impregnated silicas were then evaluated as catalysts in the oxidative coupling reaction in Examples 60-118. The experimental parameters and results obtained are presented in Tables 12-15.

The results of Examples 60-118 illustrate that a catalyst can be improved to afford a substantially higher selectivity by incorporation thereinto of a relatively small amount of a sodium component. This effect is most apparent after the catalyst has been heat treated. The incorporation of relatively higher amounts of the sodium component into the catalyst afford relatively less improvement of the selectivity of the catalyst and may promote instability of the catalyst.

TABLE 11

| Tube Packing | 20% PbO on 116 m²/gm Silica | | | | |
|---|---|---|---|---|---|
| Example | 55 | 56 | 57 | 58 | 59 |
| Reaction Temp. (°C.) | 748 | 795 | 849 | 839 | 856 |

TABLE 11-continued

| Tube Packing | 20% PbO on 116 m²/gm Silica | | | | |
|---|---|---|---|---|---|
| Example | 55 | 56 | 57 | 58 | 59 |
| Space Velocity | 6600 | 6600 | 6600 | 3300 | 1320 |
| $CH_4/O_2$ (mole ratio) | 20.1/1 | 20.1/1 | 20.1/1 | 21.5/1 | 24.1/1 |
| $O_2$ Conversion (mole %) | 6.1 | 26.0 | 41.7 | 73.9 | 99.9 |
| Product Selectivity | | | | | |
| CO | — | — | — | — | 10.7 |
| $CO_2$ | 16.0 | 13.7 | 13.1 | 14.4 | 20.1 |
| $C_2H_4$ | 8.8 | 8.8 | 18.2 | 28.8 | 33.4 |
| $C_2H_6$ | 51.8 | 60.0 | 56.8 | 47.9 | 34.4 |
| $C_2H_2$ | — | — | — | — | — |
| $C_3$'s | 5.1 | 5.1 | 4.8 | 4.2 | 1.5 |
| $C_4$'s | 18.4 | 12.4 | 7.2 | 4.8 | — |
| Selectivity to $C_2+$ | 84.1 | 86.3 | 87.0 | 85.7 | 69.3 |

TABLE 12

| Tube Packing | 20% PbO-Norton $SiO_2$ Containing 0% $Na_2O$ | | | |
|---|---|---|---|---|
| Example | 60 | 61 | 62 | 63 |
| Reaction Temp. (°C.) | 622 | 730 | 799 | 850 |
| Space Velocity | 1700 | 1700 | 1700 | 1700 |
| $CH_4/O_2$ (mole ratio) | 24.0 | 24.0 | 24.0 | 24.0 |
| $O_2$ conversion (mole %) | 42.7 | 99.2 | 99.2 | 99.2 |
| $CH_4$ conversion (mole %) | (1) | 3.2 | 3.8 | 5.0 |
| Product Selectivity | | | | |
| $H_2$ | (1) | — | — | — |
| CO | (1) | 21.8 | 26.9 | 22.9 |
| $CO_2$ | (1) | 50.7 | 38.5 | 25.1 |
| $C_2H_4$ | (1) | 6.3 | 13.8 | 20.7 |
| $C_2H_6$ | (1) | 19.8 | 17.4 | 18.7 |
| $C_2H_2$ | (1) | — | — | 0.5 |
| $C_3H_8$ | (1) | 1.3 | 0.6 | 1.0 |
| $C_3H_6$ | (1) | 1.3 | 0.6 | 1.0 |
| $i$-$C_4$ | (1) | — | — | — |
| $n$-$C_4$ | (1) | — | — | — |
| $l$-$C_4=$ | (1) | — | — | 2.5 |
| Unidentified $C_4$ | (1) | — | 2.9 | 8.6 |
| Benzene | (1) | — | — | — |
| Selectivity to $C_2+$ | (1) | 27.4 | 34.7 | 52.0 |
| Yield of $C_2+$ | (1) | 0.88 | 1.32 | 2.60 |
| $C_2H_4/C_2H_6$ (mole ratio) | 0 | 0.321 | 0.793 | 1.112 |

(1) Conversion was too low to obtain accurate selectivity measurements.

TABLE 13

| Tube Packing | 20% PbO-Norton $SiO_2$ Containing 0.67% $Na_2O$ | | | | |
|---|---|---|---|---|---|
| Example | 64 | 65 | 66 | 67 | 68 |
| Reaction Temp. (°C.) | 566 | 609 | 633 | 674 | 714 |
| Space Velocity | 1696 | 1696 | 1696 | 1696 | 1696 |
| $CH_4/O_2$ (mole ratio) | 33.3 | 33.3 | 33.3 | 33.3 | 33.3 |
| $O_2$ conversion (mole %) | 85.1 | 98.8 | 99.3 | 98.7 | 99.5 |
| $CH_4$ conversion (mole %) | 1.3 | 2.3 | 2.5 | 3.5 | 4.6 |
| Product Selectivity | | | | | |
| $H_2$ | — | — | — | — | — |
| CO | — | — | — | — | — |
| $CO_2$ | 89.5 | 60.9 | 53.5 | 42.6 | 47.2 |
| $C_2H_4$ | — | 6.3 | 11.7 | 21.6 | 29.5 |
| $C_2H_6$ | 10.5 | 29.9 | 32.4 | 27.7 | 18.2 |
| $C_2H_2$ | — | — | — | — | — |
| $C_3H_8$ & $C_3H_6$ | — | 1.4 | 1.9 | 2.0 | 3.1 |
| $i$-$C_4$ | — | — | — | — | — |
| $n$-$C_4$ | — | — | 0.2 | 0.8 | 1.8 |
| $l$-$C_4=$ | — | 1.5 | 0.4 | 5.3 | 0.1 |
| Unidentified $C_4$ | — | — | — | — | — |
| Benzene | — | — | — | — | — |
| Selectivity to $C_2+$ | 10.5 | 39.1 | 46.6 | 57.4 | 52.7 |
| Yield of $C_2+$ | 0.14 | 0.90 | 1.17 | 2.01 | 2.42 |

TABLE 13-continued

| Tube Packing | 20% PbO-Norton $SiO_2$ Containing 0.67% $Na_2O$ | | | | |
|---|---|---|---|---|---|
| $C_2H_4/C_2H_6$ (mole ratio) | 0 | 0.266 | 0.360 | 0.780 | 1.621 |
| Example | 69 | 70 | 71 | 72 | 73 |
| Reaction Temp. (°C.) | 770 | 784 | 816 | 840 | 853 |
| Space Velocity | 1696 | 1696 | 1696 | 1696 | 1696 |
| $CH_4/O_2$ (mole ratio) | 33.3 | 30.6 | 30.6 | 30.6 | 30.6 |
| $O_2$ conversion (mole %) | 99.3 | 99.5 | 99.3 | 99.5 | 99.4 |
| $CH_4$ conversion (mole %) | 4.5 | 5.0 | 6.1 | 6.0 | 6.3 |
| Product Selectivity | | | | | |
| $H_2$ | — | — | — | — | 11.0 |
| CO | — | 3.7 | 1.1 | 3.0 | 2.8 |
| $CO_2$ | 42.6 | 18.8 | 13.9 | 9.7 | 11.7 |
| $C_2H_4$ | 30.7 | 24.0 | 30.8 | 33.3 | 35.8 |
| $C_2H_6$ | 10.9 | 49.5 | 48.1 | 47.1 | 42.5 |
| $C_2H_2$ | — | 1.0 | 0.7 | 0.9 | 1.2 |
| $C_3H_8$ & $C_3H_6$ | 2.1 | 2.1 | 2.7 | 3.2 | 3.4 |
| $i$-$C_4$ | — | — | — | — | — |
| $n$-$C_4$ | 2.8 | 0.4 | 1.5 | 1.3 | 1.3 |
| $l$-$C_4=$ | 0.1 | 0.4 | 1.1 | 1.6 | 1.3 |
| Unidentified $C_4$ | — | — | — | — | — |
| Benzene | 10.2 | — | — | — | — |
| Selectivity to $C_2+$ | 57.4 | 77.4 | 84.9 | 87.4 | 85.5 |
| Yield of $C_2+$ | 2.58 | 3.87 | 5.18 | 5.24 | 5.39 |
| $C_2H_4/C_2H_6$ (mole ratio) | 2.808 | 0.485 | 0.639 | 0.707 | 0.842 |
| Example | 74 | 75 | 76 | 77 | 78 |
| Reaction Temp. (°C.) | 850 | 847 | 851 | 845 | 861 |
| Space Velocity | 1696 | 3300 | 3390 | 3390 | 3390 |
| $CH_4/O_2$ (mole ratio) | 30.6 | 24.5 | 24.5 | 24.8 | 24.8 |
| $O_2$ conversion (mole %) | 99.5 | 99.4 | 99.4 | 77.4 | 94.7 |
| $CH_4$ conversion (mole %) | 6.2 | 6.8 | 6.1 | 5.5 | 6.5 |
| Product Selectivity | | | | | |
| $H_2$ | 10.9 | 8.1 | 1.7 | — | — |
| CO | 3.7 | 5.2 | 3.4 | 2.5 | 2.5 |
| $CO_2$ | 10.6 | 12.5 | 12.5 | 13.0 | 10.4 |
| $C_2H_4$ | 33.8 | 33.7 | 26.8 | 25.5 | 30.5 |
| $C_2H_6$ | 44.3 | 41.3 | 51.6 | 54.0 | 51.3 |
| $C_2H_2$ | 1.0 | 0.9 | 0.7 | 0.8 | 0.3 |
| $C_3H_8$ & $C_3H_6$ | 3.4 | 3.3 | 2.7 | 3.1 | 3.5 |
| $i$-$C_4$ | — | — | — | — | — |
| $n$-$C_4$ | 1.2 | 1.4 | 1.0 | 0.5 | 0.8 |
| $l$-$C_4=$ | 1.9 | 1.7 | 1.3 | 0.5 | 0.8 |
| Unidentified $C_4$ | — | — | — | — | — |
| Benzene | — | — | — | — | — |
| Selectivity to $C_2+$ | 85.6 | 82.3 | 84.1 | 84.4 | 87.2 |
| Yield of $C_2+$ | 5.31 | 5.60 | 5.13 | 4.64 | 5.67 |
| $C_2H_4/C_2H_6$ (mole ratio) | 0.764 | 0.815 | 0.520 | 0.473 | 0.595 |
| Example | 79 | 80 | 81 | 82 | 83 |
| Reaction Temp. (°C.) | 865 | 855 | 843 | 869 | 871 |
| Space Velocity | 3390 | 3390 | 3390 | 3390 | 3390 |
| $CH_4/O_2$ (mole ratio) | 24.8 | 24.8 | 24.8 | 24.8 | 24.4 |
| $O_2$ conversion (mole %) | 99.6 | 98.9 | 58.0 | 88.4 | 94.1 |
| $CH_4$ conversion (mole %) | 7.4 | 7.8 | 4.3 | 6.7 | 6.5 |
| Product Selectivity | | | | | |
| $H_2$ | 2.0 | 6.7 | — | 0.9 | 1.0 |
| CO | 2.9 | 2.7 | 2.0 | 2.7 | 3.6 |
| $CO_2$ | 12.1 | 10.6 | 11.8 | 13.4 | 9.2 |
| $C_2H_4$ | 32.4 | 42.1 | 24.7 | 31.4 | 33.7 |
| $C_2H_6$ | 45.4 | 38.3 | 56.4 | 44.8 | 47.4 |
| $C_2H_2$ | 1.0 | 1.4 | 1.1 | 0.6 | 0.5 |
| $C_3H_8$ & $C_3H_6$ | 3.1 | 3.3 | 3.4 | 3.6 | 3.4 |
| $i$-$C_4$ | — | — | — | — | — |
| $n$-$C_4$ | 1.7 | 1.0 | 0.3 | 1.4 | 1.0 |
| $l$-$C_4=$ | 1.3 | 0.3 | 0.3 | 2.1 | 1.2 |
| Unidentified $C_4$ | — | 0.2 | — | — | — |
| Benzene | — | — | — | — | — |
| Selectivity to $C_2+$ | 84.9 | 86.6 | 86.2 | 83.9 | 87.2 |
| Yield of $C_2+$ | 6.28 | 6.75 | 3.71 | 5.62 | 5.67 |

TABLE 13-continued

| Tube Packing | 20% PbO-Norton SiO$_2$ Containing 0.67% Na$_2$O | | | | |
|---|---|---|---|---|---|
| C$_2$H$_4$/C$_2$H$_6$ (mole ratio) | 0.712 | 1.099 | 0.437 | 0.702 | 0.712 |
| Example | 84 | 85 | 86 | 87 | 88 |
| Reaction Temp. (°C.) | 876 | 886 | 874 | 873 | 871 |
| Space Velocity | 3390 | 3390 | 3390 | 3390 | 3390 |
| CH$_4$/O$_2$ (mole ratio) | 24.4 | 24.4 | 24.4 | 24.4 | 24.4 |
| O$_2$ conversion (mole %) | 94.7 | 99.5 | 86.7 | 85.2 | 82.5 |
| CH$_4$ conversion (mole %) | 7.2 | 7.1 | 6.4 | 6.2 | 6.1 |
| Product Selectivity | | | | | |
| H$_2$ | 0.7 | 3.8 | 1.2 | 1.2 | 1.3 |
| CO | 3.4 | 3.8 | 3.3 | 3.1 | 3.2 |
| CO$_2$ | 11.6 | 8.7 | 10.5 | 9.0 | 8.7 |
| C$_2$H$_4$ | 35.3 | 36.9 | 32.2 | 33.0 | 31.6 |
| C$_2$H$_6$ | 43.5 | 41.4 | 46.8 | 48.2 | 48.0 |
| C$_2$H$_2$ | 1.0 | 1.1 | 0.6 | 0.9 | 0.6 |
| C$_3$H$_8$ & C$_3$H$_6$ | 2.9 | 3.8 | 3.3 | 3.4 | 3.2 |
| i-C$_4$ | — | 1.8 | 0.8 | — | 1.9 |
| n-C$_4$ | 1.3 | 1.5 | 1.4 | 1.3 | 1.3 |
| 1-C$_4$= | 1.1 | 1.0 | 1.1 | 1.2 | 1.4 |
| Unidentified C$_4$ | — | — | — | — | — |
| Benzene | — | — | — | — | — |
| Selectivity to C$_2$+ | 85.1 | 87.5 | 86.2 | 88.0 | 88.0 |
| Yield of C$_2$+ | 6.13 | 6.21 | 5.52 | 5.46 | 5.37 |
| C$_2$H$_4$/C$_2$H$_6$ (mole ratio) | 0.806 | 0.893 | 0.688 | 0.684 | 0.660 |
| Example | 89 | 90 | 91 | 92 | |
| Reaction Temp. (°C.) | 870 | 869 | 866 | 864 | |
| Space Velocity | 3390 | 3390 | 3390 | 3390 | |
| CH$_4$/O$_2$ (mole ratio) | 24.4 | 24.4 | 24.5 | 24.5 | |
| O$_2$ conversion (mole %) | 72.9 | 70.5 | 72.3 | 63.1 | |
| CH$_4$ conversion (mole %) | 5.8 | 5.9 | 4.7 | 4.5 | |
| Product Selectivity | | | | | |
| H$_2$ | 1.1 | 0.9 | — | — | |
| CO | 3.2 | 2.8 | 3.5 | 2.6 | |
| CO$_2$ | 10.3 | 9.9 | 9.1 | 9.1 | |
| C$_2$H$_4$ | 28.0 | 31.3 | 28.3 | 28.1 | |
| C$_2$H$_6$ | 46.5 | 45.8 | 53.0 | 53.9 | |
| C$_2$H$_2$ | 0.7 | 0.8 | 0.7 | 0.9 | |
| C$_3$H$_8$ & C$_3$H$_6$ | 2.9 | 2.7 | 3.4 | 3.3 | |
| i-C$_4$ | 6.9 | 5.7 | — | 0.9 | |
| n-C$_4$ | 0.8 | 0.5 | 2.1 | 0.5 | |
| 1-C$_4$= | 0.7 | 0.6 | — | 0.7 | |
| Unidentified C$_4$ | — | — | — | — | |
| Benzene | — | — | — | — | |
| Selectivity to C$_2$+ | 86.5 | 87.4 | 87.5 | 88.3 | |
| Yield of C$_2$+ | 5.02 | 5.17 | 4.11 | 3.97 | |
| C$_2$H$_4$/C$_2$H$_6$ (mole ratio) | 0.602 | 0.683 | 0.533 | 0.520 | |
| Example | 93 | 94 | | | |
| Reaction Temp. (°C.) | 872 | 854 | | | |
| Space Velocity | 3390 | 3390 | | | |
| CH$_4$/O$_2$ (mole ratio) | 24.5 | 24.5 | | | |
| O$_2$ conversion (mole %) | 70.9 | 57.6 | | | |
| CH$_4$ conversion (mole %) | 5.6 | 4.5 | | | |
| Product Selectivity | | | | | |
| H$_2$ | 1.2 | — | | | |
| CO | 3.0 | 2.4 | | | |
| CO$_2$ | 8.1 | 8.7 | | | |
| C$_2$H$_4$ | 28.2 | 27.3 | | | |
| C$_2$H$_6$ | 47.3 | 53.2 | | | |
| C$_2$H$_2$ | 0.9 | 0.2 | | | |
| C$_3$H$_8$ & C$_3$H$_6$ | 3.2 | 3.5 | | | |
| i-C$_4$ | 7.4 | 3.7 | | | |
| n-C$_4$ | 1.2 | 0.5 | | | |
| 1-C$_4$= | 0.6 | 0.5 | | | |
| Unidentified C$_4$ | — | — | | | |
| Benzene | — | — | | | |
| Selectivity to C$_2$+ | 88.8 | 88.9 | | | |
| Yield of C$_2$+ | 4.97 | 4.00 | | | |
| C$_2$H$_4$/C$_2$H$_6$ (mole ratio) | 0.596 | 0.513 | | | |

TABLE 14

| Tube Packing | 20% PbO-Norton SiO$_2$ Containing 1.35% Na$_2$O | | | |
|---|---|---|---|---|
| Example | 95 | 96 | 97 | 98 |
| Reaction Temp. (°C.) | 570 | 642 | 695 | 694 |
| Space Velocity | 1696 | 1696 | 1696 | 1696 |
| CH$_4$/O$_2$ (mole ratio) | 30.0 | 30.0 | 30.0 | 30.0 |
| O$_2$ conversion (mole %) | 3.0 | 58.9 | 92.8 | 87.8 |
| CH$_4$ conversion (mole %) | .04 | 1.5 | 4.0 | 3.9 |
| Product Selectivity | | | | |
| H$_2$ | — | — | — | — |
| CO | — | — | — | — |
| CO$_2$ | 100 | 59.3 | 24.8 | 22.0 |
| C$_2$H$_4$ | (1) | 7.5 | 25.0 | 24.6 |
| C$_2$H$_6$ | (1) | 32.9 | 46.8 | 46.5 |
| C$_2$H$_2$ | (1) | — | — | — |
| C$_3$H$_8$ & C$_3$H$_6$ | (1) | 0.3 | 1.8 | 2.2 |
| i-C$_4$ | (1) | — | 0.6 | 1.3 |
| n-C$_4$ | (1) | — | 1.0 | 2.5 |
| 1-C$_4$= | (1) | — | — | 0.9 |
| Unidentified C$_4$ | (1) | — | — | — |
| Unidentified C$_6$ | (1) | — | — | — |
| Selectivity to C$_2$+ | (1) | 40.7 | 75.2 | 78.0 |
| Yield of C$_2$+ | (1) | 0.61 | 3.01 | 3.04 |
| C$_2$H$_4$/C$_2$H$_6$ (mole ratio) | (1) | 0.229 | 0.534 | 0.530 |
| Example | 99 | 100 | 101 | 102 |
| Reaction Temp. (°C.) | 690 | 684 | 682 | 723 |
| Space Velocity | 1696 | 1696 | 1696 | 1696 |
| CH$_4$/O$_2$ (mole ratio) | 30.0 | 30.0 | 30.0 | 30.0 |
| O$_2$ conversion (mole %) | 82.5 | 75.8 | 70.6 | 99.5 |
| CH$_4$ conversion (mole %) | 3.7 | 3.2 | 2.9 | 5.3 |
| Product Selectivity | | | | |
| H$_2$ | — | — | — | — |
| CO | — | — | — | — |
| CO$_2$ | 21.8 | 23.4 | 23.9 | 17.7 |
| C$_2$H$_4$ | 25.0 | 23.3 | 22.3 | 35.9 |
| C$_2$H$_6$ | 47.2 | 50.4 | 51.1 | 40.9 |
| C$_2$H$_2$ | — | — | — | — |
| C$_3$H$_8$ & C$_3$H$_6$ | 1.9 | 1.8 | 1.6 | 2.6 |
| i-C$_4$ | 2.6 | — | — | — |
| n-C$_4$ | 1.2 | 0.8 | 0.7 | 2.6 |
| 1-C$_4$= | 0.4 | 0.3 | 0.3 | 0.3 |
| Unidentified C$_4$ | — | — | — | — |
| Unidentified C$_6$ | — | — | — | — |
| Selectivity to C$_2$+ | 78.3 | 76.6 | 76.0 | 82.3 |
| Yield of C$_2$+ | 2.90 | 2.45 | 2.20 | 4.36 |
| C$_2$H$_4$/C$_2$H$_6$ (mole ratio) | 0.530 | 0.462 | 0.437 | 0.879 |
| Example | 103 | 104 | 105 | 106 | 107 |
| Reaction Temp. (°C.) | 624 | 673 | 715 | 733 | 789 |
| Space Velocity | 1696 | 1696 | 1696 | 1696 | 1696 |
| CH$_4$/O$_2$ (mole ratio) | 29.9 | 29.9 | 29.9 | 29.9 | 29.9 |
| O$_2$ conversion (mole %) | 8.6 | 99.1 | 99.1 | 98.8 | 99.4 |
| CH$_4$ conversion (mole %) | 0.2 | 3.7 | 4.6 | 4.7 | 9.5 |
| Product Selectivity | | | | | |
| H$_2$ | — | — | — | — | — |
| CO | — | Present | — | — | — |
| CO$_2$ | 56.4 | 26.3 | 29.9 | 23.5 | 32.5 |
| C$_2$H$_4$ | 7.2 | 28.4 | 36.4 | 34.6 | 27.3 |
| C$_2$H$_6$ | 36.4 | 38.8 | 27.3 | 23.8 | 8.4 |
| C$_2$H$_2$ | — | 1.2 | — | — | — |
| C$_3$H$_8$ & C$_3$H$_6$ | — | 2.9 | 2.8 | 2.7 | 2.3 |
| i-C$_4$ | — | — | — | — | 0.2 |
| n-C$_4$ | — | — | — | — | — |

TABLE 14-continued

| Tube Packing | 20% PbO-Norton SiO$_2$ Containing 1.35% Na$_2$O | | | | |
|---|---|---|---|---|---|
| l-C$_4$= | — | 0.2 | 0.3 | 0.3 | — |
| Unidentified C$_4$ | — | — | 3.3 | 3.3 | 2.6 |
| Unidentified C$_6$ | — | — | — | 11.9[2] | 26.7[3] |
| Selectivity to C$_2$+ | 43.6 | 73.6 | 70.1 | 76.6 | 67.5 |
| Yield of C$_2$+ | 0.09 | 2.72 | 3.22 | 3.60 | 6.41 |
| C$_2$H$_4$/C$_2$H$_6$ (mole ratio) | 0.200 | 0.731 | 1.332 | 1.453 | 3.288 |

(1) Conversion was too low for accurate measurements.
[2] Benzene and Toluene
[3] Approximately 65% benzene

TABLE 15

| | Example | | | |
|---|---|---|---|---|
| | 108 | 109 | 110 | 111 |
| Tube Packing | 20% PbO-Norton SiO$_2$ Containing 1.66% MgO | | | |
| Reaction Temp. (°C.) | 658 | 706 | 757 | 807 |
| Space Velocity | 1696 | 1696 | 1696 | 1696 |
| CH$_4$/O$_2$ (mole ratio) | 31.3 | 31.3 | 31.3 | 31.3 |
| O$_2$ conversion (mole %) | 48.9 | 77.3 | 99.5 | 99.5 |
| CH$_4$ conversion (mole %) | 0.8 | 1.8 | 2.2 | 2.6 |
| Product Selectivity | | | | |
| H$_2$ | 26.2 | 3.2 | 3.0 | 13.9 |
| CO | — | 21.8 | 38.6 | 34.5 |
| CO$_2$ | 80.0 | 54.9 | 40.5 | 34.3 |
| C$_2$H$_4$ | 4.4 | 8.4 | 6.0 | 11.9 |
| C$_2$H$_6$ | 15.6 | 14.9 | 12.7 | 16.2 |
| C$_3$H$_8$ & C$_3$H$_6$ | — | — | 1.1 | 1.2 |
| i-C$_4$ | — | — | — | — |
| n-C$_4$ | — | — | — | 0.2 |
| l-C$_4$ = | — | — | — | — |
| Selectivity to C$_2$+ | 20.0 | 23.3 | 21.0 | 31.2 |
| Yield of C$_2$+ | 0.32 | 0.42 | 0.46 | 0.81 |
| C$_2$H$_4$/C$_2$H$_6$ (mole ratio) | 0.283 | 0.565 | 0.471 | 0.734 |

| | Example | | | |
|---|---|---|---|---|
| | 112 | 113 | 114 | 115 |
| Tube packing | 20% PbO-Norton SiO$_2$ Containing 1.66% MgO | | | |
| Reaction Temp. (°C.) | 853 | 876 | 876 | 785 |
| Space Velocity | 1696 | 1696 | 1696 | 3390 |
| CH$_4$/O$_2$ (mole ratio) | 31.3 | 31.3 | 31.3 | 24.2 |
| O$_2$ conversion (mole %) | 99.5 | 99.5 | 99.5 | 99.5 |
| CH$_4$ conversion (mole %) | 3.0 | 3.0 | 3.3 | 3.2 |
| Product Selectivity | | | | |
| H$_2$ | 47.2 | 70.8 | 63.4 | 4.2 |
| CO | 35.4 | 38.2 | 37.7 | 31.7 |
| CO$_2$ | 25.3 | 20.0 | 22.7 | 49.0 |
| C$_2$H$_4$ | 16.7 | 20.1 | 21.2 | 5.2 |
| C$_2$H$_6$ | 16.3 | 17.2 | 14.2 | 11.4 |
| C$_3$H$_8$ & C$_3$H$_6$ | 1.6 | 2.2 | 1.7 | 1.0 |
| i-C$_4$ | — | — | 0.4 | 0.2 |
| n-C$_4$ | 2.9 | 0.2 | — | 0.2 |
| l-C$_4$ = | — | 0.2 | 0.3 | — |
| Selectivity to C$_2$+ | 39.3 | 41.8 | 39.8 | 19.3 |
| Yield of C$_2$+ | 1.18 | 1.25 | 1.31 | 0.62 |
| C$_2$H$_4$/C$_2$H$_6$ (mole ratio) | 1.028 | 1.319 | 1.495 | 0.465 |

| | Example | | |
|---|---|---|---|
| | 116 | 117 | 118 |
| Tube Packing | 20% PbO-Norton SiO$_2$ Containing 1.66% MgO | | |
| Reaction Temp. (°C.) | 691 | 810 | 863 |
| Space Velocity | 3390 | 3390 | 3390 |
| CH$_4$/O$_2$ (mole ratio) | 24.2 | 24.2 | 24.2 |
| O$_2$ conversion (mole %) | 33.2 | 99.6 | 99.5 |
| CH$_4$ conversion (mole %) | 1.0 | 3.4 | 3.6 |
| Product Selectivity | | | |
| H$_2$ | 15.0 | 2.1 | 12.9 |
| CO | 8.6 | 32.6 | 42.9 |
| CO$_2$ | 59.0 | 36.6 | 21.4 |
| C$_2$H$_4$ | 7.2 | 10.4 | 10.6 |
| C$_2$H$_6$ | 15.7 | 17.3 | 19.1 |
| C$_3$H$_8$ & C$_3$H$_6$ | 5.0 | 1.1 | 0.6 |
| i-C$_4$ | — | — | — |
| n-C$_4$ | — | 0.1 | — |
| l-C$_4$ = | — | — | 5.1 |
| Selectivity to C$_2$+ | 32.3 | 30.7 | 35.7 |
| Yield of C$_2$+ | 0.32 | 1.04 | 1.28 |
| C$_2$H$_4$/C$_2$H$_6$ (mole ratio) | 0.467 | 0.601 | 0.555 |

Additional experiments have shown that the incorporation of lithium, potassium or cesium components also affords improved selectivities of the catalysts in the oxidative coupling reaction. By contrast, incorporation of an alkaline earth metal component into the catalyst was not beneficial. Higher C$_2$H$_4$:C$_2$H$_6$ mole ratios are desirable in order to increase the yield of aromatics formed by the oligomerization of ethylene in a subsequent step, as described hereinbelow in connection with Examples 169-187.

The level of metal component on the support was found to be important within broad ranges. As can be seen from Examples 119-127, all levels of lead oxide on Calsicat D silica were effective when compared with Calsicat D silica without lead oxide (Examples 5-10). However, the low levels of lead oxide, particularly 5.9%, tend to form some carbon monoxide at 800° C. as did the base silica itself, while the higher levels of lead oxide made less or none at all.

One problem with the use of lead oxide on silica is its tendency to deactivate. As illustrated in Table 10, most preferably the support is calcined before impregnating with the reducible metal component to obtain a catalyst of the highest selectivity. However, it is also high desirable to calcine the catalyst containing the reducible metal component at high temperature in the presence of oxygen to maintain a highly stable catalyst. Examples 128-136 illustrate the influence of calcination after impregnation on catalyst performance. Without air calcination (Examples 128-130), activity and selectivity were high, but prolonged use of the catalyst above 800° C caused the catalyst to deactivate. When calcined in air at 1000° C. for 16 hours (Examples 131-133), the catalyst showed surprisingly good activity and selectivity and could be used for prolonged periods with little loss of activity. Calcination in air at 1000° C. for sixty hours (Examples 134-136) likewise provided a highly selective and stable catalyst, although some of its original activity was lost, particularly at low coupling temperatures. It is believed that lead oxide in calcination reacts with the silica base to form some form of lead silicate. In the presence of air this compound presumably is maintained in its highest valence state.

TABLE 16

| | Example | | | | |
|---|---|---|---|---|---|
| | 119 | 120 | 121 | 122 | 123 |
| | Tube Packing | | | | |

TABLE 16-continued

| | Lead Oxide on Calsicat D Silica PbO level (wt %) | | | | |
|---|---|---|---|---|---|
| | 5.9% | | | 11.1% | |
| Reaction Temp. (°C.) | 747 | 802 | 839 | 757 | 801 |
| Space Velocity | 1695 | 1695 | 1695 | 1695 | 1695 |
| $CH_4/O_2$ (mole ratio) | 23.5/1 | 23.5/1 | 23.5/1 | 23.7/1 | 23.7/1 |
| $O_2$ Conversion (mole %) | 72.2 | 99.1 | 99.3 | 60.8 | 69.0 |
| $CH_4$ Conversion (mole %) | 3.8 | 7.3 | 8.0 | 2.8 | 4.4 |
| Product Selectivity | | | | | |
| CO | — | 2.8 | 1.2 | — | 0.9 |
| $CO_2$ | 29.1 | 13.4 | 10.6 | 38.4 | 21.9 |
| $C_2H_4$ | 14.9 | 29.9 | 38.6 | 7.7 | 16.6 |
| $C_2H_6$ | 54.2 | 50.4 | 44.4 | 50.9 | 58.8 |
| $C_2H_2$ | — | 0.9 | 1.4 | — | 0.1 |
| $C_3$'s | 1.8 | 2.6 | 3.4 | 3.0 | 1.7 |
| $C_4$'s and higher | | 0.1 | 0.3 | — | — |
| Selectivity to $C_2+$ | 70.9 | 83.9 | 88.1 | 61.6 | 77.2 |
| Yield of $C_2+$ | 2.7 | 6.1 | 7.0 | 1.7 | 3.4 |

| | Example | | | |
|---|---|---|---|---|
| | 124 | 125 | 126 | 127 |
| | Tube Packing | | | |
| | Lead Oxide on Calsicat D Silica PbO level (wt %) | | | |
| | 11.1% | 33.3% | | |
| Reaction Temp. (°C.) | 837 | 757 | 801 | 837 |
| Space Velocity | 1695 | 1695 | 1695 | 1695 |
| $CH_4/O_2$ (mole ratio) | 23.7/1 | 24.0/1 | 24.0/1 | 24.0/1 |
| $O_2$ Conversion (mole %) | 99.1 | 47.7 | 67.3 | 99.0 |
| $CH_4$ Conversion (mole %) | 7.6 | 3.7 | 5.4 | 7.2 |
| Product Selectivity | | | | |
| CO | 1.7 | — | — | — |
| $CO_2$ | 12.6 | 13.6 | 10.2 | 10.1 |
| $C_2H_4$ | 31.1 | 18.5 | 29.2 | 37.1 |
| $C_2H_6$ | 51.1 | 65.7 | 57.1 | 46.9 |
| $C_2H_2$ | 0.9 | 0.2 | 0.4 | 0.7 |
| $C_3$'s | 2.6 | 2.1 | 2.9 | 3.6 |
| $C_4$'s and higher | — | — | 0.2 | — |
| Selectivity to $C_2+$ | 85.7 | 86.5 | 89.8 | 88.3 |
| Yield of $C_2+$ | 6.5 | 3.2 | 4.8 | 6.4 |

TABLE 17

| | Example | | | | |
|---|---|---|---|---|---|
| | 128 | 129 | 130 | 131 | 132 |
| Calcination Temp. (°C.) | 600 | 600 | 600 | 1000 | 1000 |
| Calcination Time (hr) | 16 | 16 | 16 | 16 | 16 |
| Air | no | no | no | yes | yes |
| Reaction Temp. (°C.) | 721 | 807 | 822 | 745 | 831 |
| Space Velocity | 1700 | 1700 | 1700 | 1700 | 1700 |
| $CH_4/O_2$ (mole rate) | 18.5/1 | 18.5/1 | 18.5/1 | 23.4/1 | 23.4/1 |
| $O_2$ Conversion (mole %) | 71.1 | 95.2 | 95.0 | 68.7 | 99.5 |
| $CH_4$ Conversion (mole %) | | | | 4.5 | 9.0 |
| Product Selectivity | | | | | |
| CO | — | — | 1.8 | — | 1.5 |
| $CO_2$ | 21.1 | 14.0 | 12.7 | 20.9 | 9.7 |
| $C_2H_4$ | 14.8 | 36.3 | 42.2 | 17.8 | 34.1 |
| $C_2H_6$ | 39.4 | 44.7 | 30.9 | 59.6 | 41.7 |
| $C_2H_2$ | — | — | 0.7 | — | 0.4 |
| $C_3$'s | 4.1 | 3.2 | 4.7 | 1.6 | 2.9 |
| $C_4$'s and higher | 20.7 | 1.7 | 7.1 | — | 11.4 |
| Selectivity to $C_2+$ | 79.0 | 85.9 | 85.6 | 79.0 | 90.5 |
| Yield of $C_2+$ | | | | 3.6 | 8.1 |

| | Example | | | |
|---|---|---|---|---|
| | 133 | 134 | 135 | 136 |
| Calcination Temp. (°C.) | 1000 | 1000 | 1000 | 1000 |
| Calcination Time (hr) | 16 | 60 | 60 | 60 |
| Air | yes | yes | yes | yes |
| Reaction Temp. | 856 | 723 | 825 | 863 |
| Space Velocity | 1700 | 1700 | 1700 | 1700 |

TABLE 17-continued

| | | | | |
|---|---|---|---|---|
| $CH_4/O_2$ (mole ratio) | 23.4/1 | 24.2/1 | 24.2/1 | 24.3/1 |
| $O_2$ Conversion (mole %) | 99.5 | 9.7 | 68.5 | 99.1 |
| $CH_4$ Conversion (mole %) | 8.2 | 0.7 | 5.5 | 7.4 |
| Product Selectivity | | | | |
| CO | — | — | 2.5 | 3.8 |
| $CO_2$ | 10.2 | 15.2 | 9.5 | 8.5 |
| $C_2H_4$ | 43.2 | 5.4 | 31.8 | 42.1 |
| $C_2H_6$ | 39.9 | 72.0 | 52.0 | 39.9 |
| $C_2H_2$ | — | — | 1.3 | 1.7 |
| $C_3$'s | 3.8 | 7.5 | 2.9 | 3.7 |
| $C_4$'s and higher | 1.0 | — | — | 0.4 |
| Selectivity to $C_2^+$ | 87.9 | 84.9 | 88.0 | 87.8 |
| Yield of $C_2^+$ | 7.2 | 5.9 | 4.8 | 6.5 | and stable catalyst, although some of its original activity was lost, particularly at low coupling temperatures. It is believed that lead oxide in calcination reacts with the silica base to form some form of lead silicate. In the presence of air this compound presumably is maintained in its highest valence state.

The conditions employed to calcine the oxidative coupling catalysts employed in Examples 5-27 and 32-187 are summarized in Table 18.

Other lead compounds have been shown to give good selectivities for the formation of coupled products, depending on the nature of the anion. Lead sulfate (Examples 137-141) was relatively unattractive until it was exposed to prolonged reaction conditions. During this period. $SO_2$ was evolved making a new and more selective species. Lead sulfide (Examples 142-144) was active from the beginning and afforded high selectivity for the formation of coupled products but tended to deactivate with time. Lead tungstate (Examples 145-147) was moderately selective at low temperatures. Lead molybdate (Examples 148-149) was much less selective even at low temperatures. In each of Examples 137-149, the lead compound was supported on a Calsicat D support. Preferred anions are those that can decompose to form a lead oxide type of compound.

Catalysts containing compounds of reducible metals other than lead are less selective when tested in the oxidative coupling reaction under similar conditions. For example, vanadia on Calsicat D silica afforded only a 22% selectivity for the formation of coupled products. Manganese oxide on Calsicat D silica afforded 50-64% selectivity for the formation of coupled products. Indium oxide on Calsicat D silica afforded a 31-45% selectivity for the formation of coupled products.

TABLE 18

| Example | Conditions of Calcination Before Impregnation | Surface Area ($m^2/gm$) Before Impregnation | Conditions of Calcination After Impregnation |
|---|---|---|---|
| 5-10[1] | 8 hrs at 1000° C. | 24 | |
| 11-13[1] | Used as received | <5 | |
| 14-17 | Used as received | 24 | |
| 18-21[1] | 2 hrs at 600° C. | <5 | |
| 22-25[1] | 2 hrs at 600° C. | 44 | |
| 26[1] | 2 hrs at 600° C. | — | |
| 27[1] | 2 hrs at 600° C. | — | |
| 32-35[1] | 2 hrs at 743° C. | — | |
| 36-38 | — | 4 | 2 hrs at 600° C. |
| 39-46 | Used as received | 24 | 2 hrs at 600° C. |
| 47-49 | Used as received | 245 | 2 hrs at 600° C. |
| 50 | 2 hrs at 650° C. | 239 | 2 hrs at 600° C. |
| 51 | 8 hrs at 830° C. | 179 | 2 hrs at 600° C. |
| 52 | 8 hrs at 920° C. | 116 | 2 hrs at 600° C. |
| 53 | 8 hrs at 970° C. | 21 | 2 hrs at 600° C. |
| 54 | 4 hrs at 1000° C. | <2 | 2 hrs at 600° C. |
| 55-59 | 8 hrs at 920° C. | 116 | 2 hrs at 600° C. |
| 60-118 | 2-3 hrs at 550-660° C. | — | 2 hrs at 600° C. |
| 119-127 | Used as received | 24 | 2 hrs at 600° C. |
| 128-130 | Used as received | 24 | 16 hrs at 600° C. |
| 131-133 | Used as received | 5[2] | 16 hrs at 1000° C. |
| 134-136 | Used as received | 4[2] | 60 hrs at 1000° C. |
| 137-168 | Used as received | 24 | 2 hrs at 600° C. |
| 181-188 | Used as received | 24 | 2 hrs at 600° C. |

[1]Not impregnated
[2]Surface area after impregnation

TABLE 19

| | Example | | | | |
|---|---|---|---|---|---|
| | 137 | 138 | 139 | 140 | 141 |
| | Tube Packing | | | | |
| | 20% $PbSO_4$ | | | | |
| Reaction Temp. (°C.) | 715 | 756 | 803 | 842 | 830 |
| Space Velocity | 1695 | 1695 | 1695 | 1695 | 3390 |
| $CH_4/O_2$ (mole ratio) | 22.7/1 | 22.7/1 | 22.7/1 | 22.8/1 | 22.1/1 |
| $O_2$ Conversion (mole %) | 99.4 | 99.3 | 99.4 | 99.2 | 99.4 |
| $CH_4$ Conversion (mole %) | 8.5 | 7.3 | 6.9 | 7.3 | 8.3 |
| Product Selectivity | | | | | |
| CO | — | — | 0.3 | 1.7 | 3.4 |
| $CO_2$ | 58.5 | 31.9 | 19.9 | 17.0 | 12.2 |
| $C_2H_4$ | 7.3 | 16.7 | 30.5 | 42.7 | 32.9 |
| $C_2H_6$ | 28.6 | 36.7 | 45.5 | 32.8 | 47.6 |
| $C_2H_2$ | — | — | 0.6 | 0.5 | 0.7 |
| $C_3$'s | 1.0 | 2.4 | 2.3 | 4.0 | 2.9 |
| $C_4$'s+ | 4.6 | 12.3 | 0.9 | 1.3 | 0.2 |
| Selectivity to $C_2^+$ | 41.5 | 68.1 | 79.8 | 81.3 | 84.3 |
| Yield of $C_2^+$ | 3.5 | 5.0 | 5.0 | 5.9 | 7.0 |
| | Example | | | | |

TABLE 19-continued

|  | 142 | 143 | 144 |
|---|---|---|---|
|  |  | Lead compound |  |
|  |  | 20% PbS |  |
| Reaction Temp. (°C.) | 757 | 805 | 858 |
| Space Velocity | 1690 | 1690 | 1690 |
| $CH_4/O_2$ (mole ratio) | 23.0/1 | 23.1/1 | 23.1/1 |
| $O_2$ Conversion (mole %) | 82.7 | 99.0 | 99.4 |
| $CH_4$ Conversion (mole %) | 6.4 | 7.3 | 8.7 |
| Product Selectivity |  |  |  |
| CO | — | — | — |
| $CO_2$ | 20.5 | 13.1 | 10.3 |
| $C_2H_4$ | 19.4 | 32.6 | 42.2 |
| $C_2H_6$ | 55.6 | 51.2 | 34.6 |
| $C_2H_2$ | 0.1 | 0.4 | 2.3 |
| $C_3$'s | 1.8 | 2.8 | 4.3 |
| $C_4$'s+ | 1.2 | — | 6.4 |
| Selectivity to $C_2^+$ | 78.1 | 87.0 | 89.8 |
| Yield of $C_2^+$ | 5.0 | 6.4 | 7.8 |

|  | Example |  |  |  |  |
|---|---|---|---|---|---|
|  | 145 | 146 | 147 | 148 | 149 |
|  |  |  | Tube Packing |  |  |
|  | 20% $PbWO_4$ |  |  | 20% $PbMoO_4$ |  |
| Reaction Temp. (°C.) | 742 | 807 | 879 | 763 | 863 |
| Space Velocity | 3390 | 3390 | 3390 | 1695 | 1695 |
| $CH_4/O_2$ (mole ratio) | 22.3/1 | 22.3/1 | 22.3/1 | 23.8/1 | 23.8/1 |
| $O_2$ Conversion (mole %) | 62.4 | 99.3 | 99.1 | 99.4 | 99.0 |
| $CH_4$ Conversion (mole %) | 3.2 | 5.4 | 7.3 | 3.6 | 4.7 |
| Product Selectivity |  |  |  |  |  |
| CO | — | 7.4 | 44.5 | 6.7 | 43.9 |
| $CO_2$ | 36.5 | 36.1 | 26.7 | 65.5 | 40.3 |
| $C_2H_4$ | 8.1 | 12.3 | 5.4 | 2.6 | 2.7 |
| $C_2H_6$ | 51.1 | 42.4 | 21.4 | 24.6 | 10.8 |
| $C_2H_2$ | 1.5 | — | 0.9 | — | 1.6 |
| $C_3$'s | 2.2 | 1.8 | 1.0 | 0.6 | 0.7 |
| $C_4$'s+ | 0.7 | — | — | — | — |
| Selectivity to $C_2^+$ | 63.6 | 56.5 | 28.7 | 27.8 | 15.8 |
| Yield of $C_2^+$ | 1.9 | 3.1 | 2.1 | 1.0 | 0.7 |

EXAMPLES 150–155

All of the examples of the oxidative coupling reaction presented in Examples 1–149 were performed using a once-through operational mode, with no attempt being made to recover and recycle the unreacted feedstock alkane. In order to increase the conversion of the feedstock alkane and the yield of desired products therefrom, it is desirable to recycle unused feedstock alkane. However, the use of simple recycle of the entire product mixture formed in the oxidative coupling reaction is not particularly advantageous as shown in Examples 150–155. Examples 150–155 were performed using the same general procedure as used in Examples 39–46, except that in Examples 154–155 the product was recycled. The catalyst employed in Examples 150–155 was a Calsicat D silica support (that had not been calcined prior to impregnation) containing 20% by weight of PbO that was calcined for 2 hours at 600° C. after impregnation.

Examples 150–153 show the performance of a lead oxide catalyst on Calsicat D silica in a once-through mode. As is seen, even at the lowest $CH_4/O_2$ mole ratio of 5.2/1 (Example 153), the selectivity for the formation of coupled products was respectable, but the conversion of methane and yield of coupled products were at best only about 19% and 14%, respectively.

Surprisingly, however, when the entire gaseous product mixture from the oxidative coupling reaction was recycled to the oxidative coupling step (Examples 154–155), selectivity for the formation of coupled products dropped drastically into the range of 42–61%, even with high mole ratios of $CH_4/O_2$ in the total incoming gas, and the yield of coupled products (obtained as the product of the $CH_4$ conversion multiplied by the selectivity for the formation of coupled products, divided by 100) was no better than with once-through operations.

TABLE 20

| Example | 150 | 151 | 152 | 153 | 154 | 155 |
|---|---|---|---|---|---|---|
| Reaction Temp. (°C.) | 829 | 896 | 915 | 914 | 836 | 836 |
| Space Velocity | 6600 | 3300 | 1320 | 1320 | 1690 | 1690 |
| Recycle |  | No |  |  | Yes |  |
| $CH_4/O_2$ (mole ratio) in makeup feed | 18.7/1 | 19.9/1 | 10.3/1 | 5.2/1 | 8.4/1 | 8.4/1 |
| $CH_4/O_2$ (mole ratio) in total feed | 18.7/1 | 19.9/1 | 10.3/1 | 5.2/1 | 33.2/1 | 24.5/1 |
| $O_2$ Conversion (mole %) | 33.7 | 92.3 | 100.0 | 88.7 | 96.4 | 94.9 |
| $CH_4$ Conversion (mole %) | 3.4 | 8.5 | 13.4 | 18.7 | 9.5 | 22.0 |
| Product Selectivity |  |  |  |  |  |  |
| CO | 0.0 | 0.0 | 0.0 | 6.6 | 6.5 | 6.7 |
| $CO_2$ | 8.3 | 9.6 | 14.2 | 18.3 | 32.9 | 51.1 |
| $C_2H_4$ | 19.7 | 37.4 | 43.6 | 30.2 | 32.7 | 25.3 |
| $C_2H_6$ | 70.4 | 42.4 | 26.2 | 20.2 | 14.0 | 9.8 |
| $C_2H_2$ | 0.0 | 2.8 | 2.0 | 0.0 | 0.7 | 0.6 |
| $C_3$'s | 1.7 | 7.5 | 7.2 | 19.5 | 4.7 | 3.2 |
| $C_4$'s | 0.0 | 0.4 | 6.8 | 5.6 | 8.0 | 2.7 |
| Selectivity | 91.8 | 90.5 | 85.8 | 75.5 | 60.1 | 41.6 |

TABLE 20-continued

| Example | 150 | 151 | 152 | 153 | 154 | 155 |
|---|---|---|---|---|---|---|
| to $C_2+$ | | | | | | |
| Yield of $C_2+$ | 3.1 | 7.7 | 11.5 | 14.1 | 5.7 | 9.2 |

EXAMPLES 156-168

Examples 156-168 involve a systematic study to find the components in recycle gas that are responsible for this undesirable effect illustrated in Examples 154-155. Examples 156-168 were performed using the same general procedure as used in Examples 39-46, except as indicated herein. The catalyst employed in Examples 156-168 was a Calsicat D silica support (that had not been calcined prior to impregnation) containing 20% by weight of PbO that was calcined for 2 hours at 600° C. after impregnation. By spiking methane feed to the oxidative coupling reaction with nitrogen, carbon monoxide, carbon dioxide and water, it was observed that none of these materials had a deleterious effect. Residual olefins and acetylene in the recycle gas, however, did have an undesirable effect in the oxidative coupling reaction. Ethane itself did not. The effect of ethane in the oxidative coupling reaction is shown in Examples 156-161. The use of blend of 10% ethane and 90% methane as feedstock afforded a surprising increase of both selectivity and yield for ethylene and higher products. Even a 100% ethane feedstock was converted to unsaturates in high selectivity and yield. Accountability of carbons across the system was essentially 100%, indicating little tendency to form coke. On the other hand, the presence of ethylene in the feedstock to the oxidative couling reactor had a deleterious effect, even at levels of 1% in methane, as shown in Examples 162-168. Of particular concern was the observation that accountability of carbons across the system was poor, as a result of coke formation. Thus, in order to increase the degree of conversion of the feedstock alkane and the yield of the desired products therefrom, the recycle gas must be substantially free of ethylene and other higher unsaturates to preserve the high selectivity of an oxidative coupling catalyst for methane coupling, but it is advantageous that ethane is present in the feed or recycle.

TABLE 21

| Examples | 156 | 157 | 158 | 159 | 160 | 161 |
|---|---|---|---|---|---|---|
| Feed | 10% $C_2H_6$ in $CH_4$ | | | 100% $C_2H_6$ | | |
| Reaction Temp. (°C.) | 783 | 838 | 847 | 739 | 787 | 823 |
| Space Velocity | 6600 | 6600 | 3300 | 6600 | 6600 | 6600 |
| $CH_4/O_2$ (mole ratio) | 16.8/1 | 16.8/1 | 17.6/1 | — | — | — |
| $C_2H_6/O_2$ (mole ratio) | 1.76/1 | 1.76/1 | 1.89/1 | 11.5 | 11.5 | 5.4 |
| $O_2$ Conversion (mole %) | 30.0 | 85.3 | 100 | 59.2 | 100 | 100 |
| $C_2H_6$ Conversion (mole %) | 19.2 | 44.2 | 66.5 | 9.7 | 27.3 | 62.5 |
| Product Selectivity | | | | | | |
| CO | — | — | — | 0.15 | 2.1 | 3.9 |
| $CO_2$ | 6.9 | 5.4 | 3.3 | 1.3 | 0.6 | 0.8 |
| $CH_4$ | — | — | — | 2.4 | 2.9 | 5.2 |
| $C_2H_4$ | 89.6 | 89.2 | 86.2 | 92.0 | 88.2 | 84.0 |
| $C_2H_6$ | — | — | — | — | — | — |
| $C_2H_2$ | — | 0.8 | 2.3 | — | 2.5 | 3.0 |
| $C_3$'s | 3.5 | 4.7 | 6.3 | 4.1 | 1.8 | 2.2 |
| $C_4$'s | — | — | 2.0 | — | 2.0 | 0.8 |
| Selectivity to $C_2+$ | 93.1 | 94.7 | 96.8 | 96.1 | 94.5 | 90.0 |
| Yield of $C_2+$ | 17.9 | 41.9 | 64.3 | 9.3 | 25.8 | 56.3 |

TABLE 22

| Example | 162 | 163 | 164 | 165 | 166 | 167 | 168 |
|---|---|---|---|---|---|---|---|
| Feed, % $C_2H_4$ in $CH_4$ | 0 | 0.8 | 1.4 | 10 | 10 | 100 | 100 |
| Temp. (°C.) | 815 | 814 | 811 | 746. | 795 | 733 | 836 |
| Space Velocity | 6600 | 6600 | 6600 | 6600 | 6600 | 6600 | 3300 |
| $CH_4/O_2$ (mole ratio) | 24.1/1 | 25.9/1 | 27.3/1 | 18.0/1 | 18.0/1 | — | — |
| $C_2H_4/O_2$ (mole ratio) | — | — | — | 2.3/1 | 2.3/1 | 16.8/1 | 2.3/1 |
| $O_2$ Conversion (mole %) | 52.6 | 64.4 | 67.3 | 85.0 | 99.7 | 71.8 | 100 |
| $C_2H_4$ Conv. (mole %) | — | — | — | 14.7 | 20.6 | 4.2 | 62.6 |
| Product Selectivity | | | | | | | |
| CO | — | — | — | 1.4 | 0.1 | 44.1 | 29.0 |
| $CO_2$ | 8.5 | 15.6 | 18.1 | 25.1 | 21.9 | ? | 16.1 |
| $CH_4$ | — | — | — | — | — | 9.0 | 16.1 |
| $C_2H_4$ | 28.0 | 15.1 | 2.4 | — | — | — | — |
| $C_2H_6$ | 47.8 | 47.9 | 61.1 | 26.0 | 27.8 | 7.9 | 4.8 |
| $C_2H_2$ | — | — | 4.3 | 4.7 | 6.2 | 5.9 | 1.9 |
| $C_3$'s | 15.8 | 17.3 | 8.9 | 9.9 | 13.8 | 26.1 | 5.6 |
| $C_4$'s+ | — | — | 5.2 | 32.9 | 30.3 | 7.0 | 20.9 |
| Selectivity to $C_2+$ | 91.6 | 80.3 | 81.9 | 73.5 | 78.1 | 46.9 | 33.2 |

EXAMPLES 169-188

It was surprisingly observed that certain acid cetalysts were able to remove ethylene and higher unsaturates from very dilute methane streams even at atmospheric pressure and that this reaction gave rise to high yields of recoverable aromatic hydrocarbons. While it had been known that metal-exchanged zeolites do oligomerize ethylene to form higher molecular weight olefins under pressure, we found that such catalysts are ineffective under conditions of low pressure and low concentration. Similarly, an alumina catalyst containing vanadium oxide and palladium and reported by A.B. Evin, et al, *J. of Catalysis*, 30, 109-117 (1973) for the oxidative conversion of ethylene to acetaldehyde, was employed in the oligomerization reaction with a synthetic mixture containing nitrogen, oxygen, methane, acetylene, ethylene, ethane and traces of $C_3$ and $C_4$ paraffins and olefins, but was found to convert only 14-56% of the ethylene at very low space velocities. When used with the same mixture in the oligomerization reaction, concentrated sulfuric acid was effective only for the conversion of higher olefins.

Only zeolitic materials in the acid-exchanged form showed appreciable activity in the oligomerization reaction. A number of the most effective materials are shown in Examples 169-180. Examples 169-176 involve a catalyst which is a composite of 35 weight percent of alumina and 65 weight percent of one of two acidic borosilicate molecular sieves made in accordance with preparations disclosed in Haddid, European patent application Ser. No. 82303246.1. A borosilicate sieve of relatively low acidity was employed in Examples 169-172. It gave good conversion of ethylene at low space velocities, complete acetylene conversion at all space velocities tested and complete or nearly complete conversion of propylene under most conditions. Although products above $C_5$ were not measured in these studies, the buildup of higher hydrocarbons was observed. A borosilicate of stronger acidity was employed in Examples 172-176 and was more effective than the less acidic borosilicate, giving 80-90% conversion of ethylene over a wide temperature range at a higher space velocity. ZSM-5, the strongest acidic zeolitic material tested, was employed in Examples 177-180 and was especially effective, giving 95-100% conversion of ethylene at space velocities in the range of 269-1440. Water was found not to be detrimental to the olefin conversion, as indicated by Examples 175-176 and 179-180.

TABLE 23

| Examples | 169 | 170 | 171 | 172 |
|---|---|---|---|---|
| Temp. (°C.) | 396 | 353 | 337 | 321 |
| Space Velocity | 191 | 96 | 49 | 44 |
| Feed Component | Percent | Percent Removed in Product[1] | | |
| $N_2$ | 48.8 | 0 | 0 | 0 | 0 |
| $CH_4$ | 47.0 | 0.4 | 0 | 0.9 | 1.6 |
| $CO_2$ | 0.49 | 0.7 | −0.9 | 0.2 | −7.2 |
| $O_2$ | 0.99 | 0.3 | −0.8 | −0.5/−1.1 | |
| $C_2H_4$ | 1.01 | 34.6 | 57.7 | 78.5 | 91.8 |
| $C_2H_6$ | 1.01 | 1.7 | 0.4 | 0.2 | −11.4 |
| $C_2H_6$ | 0.13 | 100 | 81.7 | 100 | 100 |
| $C_3H_8$ | 0.10 | 0 | 0 | 0 | −103 |
| $C_3H_6$ | 0.11 | 16.7 | 84.4 | 100 | 100 |
| $I-C_4$ | 0.11 | −72.7 | −47.8 | −83.7 | −222 |
| $N-C_4$ | 0.06 | −116 | −59.7 | −43.5 | −0.3 |
| $C_4+$ | 0.27 | −19.1 | −1.6 | 6.4 | −135 |
| Examples | 173 | 174 | 175[2] | 176[2] |
| Temp. (°C.) | 296 | 317 | 310 | 365 |
| Space Velocity | 360 | 360 | 360 | 360 |
| Feed Component | Percent | Percent removed in Product[1] | | |
| $N_2$ | 48.9 | 0 | 0 | 0 | 0 |
| $CH_4$ | 47.0 | −0.8 | −0.9 | 0.4 | −0.3 |
| $CO_2$ | 0.50 | 5.6 | 6.8 | −20.5 | −14.0 |
| $O_2$ | 1.00 | −1.0 | −1.0 | −0.8 | −0.6 |
| $C_2H_4$ | 1.00 | 79.9 | 89.9 | 88.5 | 87.3 |
| $C_2H_6$ | 1.00 | −1.8 | −2.8 | −2.3 | −3.3 |
| $C_2H_6$ | 0.01 | 100 | 100 | 100 | 100 |
| $C_3H_8$ | 0.10 | −97.1 | −150 | −74.8 | −150 |
| $C_3H_6$ | 0.10 | 100 | 93.5 | 100 | 100 |
| $I-C_4$ | 0.10 | −79.6 | −94.7 | −124.1 | −94.5 |
| $N-C_4$ | 0.10 | 24.5 | 22.0 | 18.9 | 19.7 |
| $C_4+$ | 0.10 | −9.6 | −14.5 | −29.9 | 31.4 |
| Examples | 177 | 178 | 179[2] | 180[2] |
| Temp. (°C.) | 296 | 301 | 309 | 292 |
| Space Velocity | 360 | 1440 | 720 | 1440 |
| Feed Component | Percent | Percent Removed in Product[1] | | |
| $N_2$ | 48.9 | 0 | 0 | 0 | 0 |
| $CH_4$ | 47.0 | −0.8 | −0.3 | 0.5 | 0.2 |
| $CO_2$ | 0.50 | 23.7 | 11.7 | 2.3 | 0.7 |
| $O_2$ | 1.00 | −0.4 | −0.3 | 1.6 | −1.4 |

TABLE 23-continued

| $C_2H_4$ | 1.00 | 100 | 95.0 | 99.0 | 96.1 |
|---|---|---|---|---|---|
| $C_2H_6$ | 1.00 | −1.3 | −0.7 | −2.4 | −1.7 |
| $C_2H_6$ | 0.01 | 100 | 100 | 100 | 100 |
| $C_3H_8$ | 0.10 | −142 | −183 | −150 | −138 |
| $C_3H_6$ | 0.10 | 100 | 100 | 100 | 100 |
| $I-C_4$ | 0.10 | −172 | −152 | −179 | −161 |
| $N-C_4+$ | 0.10 | −14.5 | −30.3 | −37.8 | −2.3 |

[1]A negative value indicates an increase in that component.
[2]Water was added with the feed at about 10 moles per mole of ethylene.

To show the effect of the oligomerization of unsaturates of recycle to the oxidative coupling reaction, a packed column of H-ZSM-5 was employed in Examples 181-189 at the outlet of the oxidative coupling reactor to oligomerize the unsaturates in the product stream, higher products were largely removed with a dry-ice acetone trap, and the remaining gases were recycled back to the oxidative coupling reactor. The oxidative coupling catalyst employed was a Calsicat D silica support (which had not been calcined prior to being impregnated) containing 20 percent by weight of lead oxide and which had been calcined in air at about 600° C. for 2 hours after impregnation.

By comparison to the results of Example 155 where olefins in the feed to the oxidative coupling reactor were not oligomerized, in Examples 181-188, there was a noticeable improvement in methane conversion, selectivity for the production of coupled products and yield of coupled products in the oxidative coupling reaction. Furthermore, liquids in large quantities were condensed out of the system.

To demonstrate that small amounts of oligomerization products and higher molecular weight coupled products remaining in the recycle after oligomerization and after the dry ice-acetone trap were detrimental to the oxidative coupling reaction, the recycle stream was passed through a bed of granular coconut charcoal after passing through the dry-ice trap and before being returned to the oxidative coupling reactor. The effect of this is seen in Examples 185-188. By the simple addition of a charcoal bed, methane conversions, selectivities for the formation of coupled products and yields of coupled products increased to 63-82%, 78-85% and 53-67%, respectively.

TABLE 24

| Example | 155 | 181 | 182 | 183 | 184 |
|---|---|---|---|---|---|
| Special Conditions | | Without Charcoal | | | |
| Oxid. Coup. Temp (°C.) | 836 | 806 | 824 | 810 | 853 |
| Oxid. Coup. Space Velocity | 1690 | 1690 | 1690 | 2618 | 1960 |
| Recycle | yes | yes | yes | yes | yes |
| Oligomerization | no | yes | yes | yes | yes |
| Olig. Temp. (°C.) | — | 285 | 285 | 285 | 285 |
| Olig. Space Velocity | — | ~1400 | ~1400 | ~1400 | ~1400 |
| $CH_4/O_2$ (mole ratio) in makeup feed | 8.4/1 | 4.2/1 | 4.0/1 | 2.3/1 | 1.43/1 |
| $CH_4/O_2$ (mole ratio) in total feed | 24.5/1 | 23.2/1 | 26.1/1 | 18.3/1 | 16.4/1 |
| $O_2$ Conversion (mole %) | 94.9 | 94.4 | 95.0 | 99.5 | 99.4 |
| $CH_2$ Conversion (mole %) | 22.0 | 32.2 | 27.9 | 49.1 | 62.9 |
| Product Selectivity | | | | | |
| CO | 6.7 | 2.2 | 0.9 | 0.8 | 1.2 |
| $CO_2$ | 51.1 | 17.2 | 15.8 | 30.5 | 35.2 |
| $C_2H_4$ | 25.3 | 0.0 | 0.1 | 0.0 | 0.2 |
| $C_2H_6$ | 9.8 | 7.6 | 7.6 | 5.9 | 3.1 |
| $C_2H_2$ | 0.6 | 0.0 | 0.0 | 0.0 | 0.0 |

TABLE 24-continued

| | | | | | |
|---|---|---|---|---|---|
| C$_3$'s | 3.7 | 0.9 | 1.8 | 1.1 | 0.7 |
| C$_4$'s | 2.7 | 3.8 | 8.8 | 2.8 | 2.1 |
| Liquids | — | 68 | 66 | 59 | 57 |
| Selectivity to C$_2$+ | 42.1 | 80.6 | 83.3 | 68.8 | 63.6 |
| Yield of C$_2$+ | 9 | 26 | 23 | 34 | 40 |

| Example | 185 | 186 | 187 | 188 |
|---|---|---|---|---|
| Special Conditions | | With Charcoal | | |
| Oxid. Coup. Temp. (°C.) | 854 | 858 | 847 | 809 |
| Oxid. Coup. Space Velocity | 2618 | 2618 | 1960 | 1940 |
| Recycle | yes | yes | yes | yes |
| Oligomerization | yes | yes | yes | yes |
| Olig. Temp. (°C.) | 285 | 285 | 285 | 285 |
| Olig. Space Velocity | ~1400 | ~1400 | ~1400 | ~1400 |
| CH$_4$/O$_2$ (mole ratio) in makeup feed | 1.92/1 | 1.92/1 | 1.52/1 | 1.47/1 |
| CH$_4$/O$_2$ (mole ratio) in total feed | 13.6/1 | 13.6/1 | 14.3/1 | 7.2/1 |
| O$_2$ Conversion (mole %) | 96.8 | 99.1 | 99.4 | 98.6 |
| CH$_4$ Conversion (mole %) | 63.1 | 64.9 | 72.5 | 81.6 |
| Product Selectivity | | | | |
| CO | 0.6 | 0.8 | 0.7 | 0.0 |
| CO$_2$ | 14.8 | 17.8 | 21.6 | 17.8 |
| C$_2$H$_4$ | 0.2 | 0.2 | 0.1 | 0.0 |
| C$_2$H$_6$ | 3.3 | 3.3 | 2.6 | 1.7 |
| C$_2$H$_2$ | 0.0 | 0.0 | 0.0 | 0.0 |
| C$_3$'s | 0.5 | 0.6 | 0.4 | 0.4 |
| C$_4$'s | 2.1 | 4.1 | 1.0 | 0.0 |
| Liquids | 79 | 53 | 56 | 67 |
| Selectivity to C$_2$+ | 84.6 | 81.4 | 77.7 | 82.2 |
| Yield of C$_2$+ | 53 | 53 | 56 | 67 |

EXAMPLE 189

Since air is added to the system in the oxidative coupling step, a slip stream of the recycle gas is vented to prevent a buildup of nitrogen in the gas that is recycled to the oxidative coupling step. The slip stream which is vented contains about 10–20% of the methane originally charged to the reactor. We have found that, by passing the slip stream through a bed of coconut charcoal, not only is the methane recovered, but also both nitrogen and carbon dioxide in the slip stream are vented and prevented from building up in the recycle gas. As a mixture of nitrogen, carbon dioxide, methane, and ethane was passed through a bed of coconut charcoal, a stream of nitrogen largely devoid of hydrocarbons passed out of the bed. As the adsorption was continued, the other components of the stream passed out of the bed in this order: methane, carbon dioxide, and ethane. When the bed became saturated with methane, methane began to pass out of the bed, and the charcoal bed was removed from service and replaced in service by a fresh charcoal bed. The components adsorbed on the saturated bed were desorbed with vacuum, in the order: methane, carbon dioxide, and ethane. Hence, by judicious use of vacuum, fractions rich in methane, carbon dioxide and ethane were isolated. The desorbed methane is returned back to the system, and nitrogen and carbon dioxide rejected, thus permitting a nearly complete return of methane to the system with high ultimate conversion and a minimal buildup of nitrogen and carbon dioxide in the system. With about a 20-minute adsorption of components from the slip stream and a 10-minute desorption of the adsorbed methane, a charcoal bed was able to be placed on a fast cycle for economic separation of components.

From the above description, it is apparent that the objects of the present invention have been achieved. While only certain embodiments have been set forth, alternative embodiments and various modifications will be apparent from the above description to those skilled in the art. These and other alternatives are considered equivalents and within the spirit and scope of the present invention.

Having described the invention, what is claimed is:

1. An oxidative coupling catalyst comprising a reducible compound selected from the group consisting of lead, antimony, vanadium, tin, bismuth, cadmium, manganese, thallium and mixtures thereof and a support comprising silica having a surface area in the range of from above about 21m$^2$/gm to about 175 m$^2$/gm, wherein the reducible compound is at a level of from about 2 to about 50 weight percent, calculated as the oxide of the reducible metal and based on the weight of the catalyst.

2. The oxidative coupling catalyst of claim 1 wherein the reducible metal compound is at a level of from about 10 to about 30 weight percent, calculated as the oxide of the reducible metal and based on the weight of the catalyst.

3. The oxidative coupling catalyst of claim 1 wherein the reducible metal compound is an oxide, sulfide, sulfate or carbonate.

4. The oxidative coupling catalyst of claim 1 comprising a reducible compound of lead.

5. The oxidative coupling catalyst of claim 4 wherein the reducible lead compound comprises lead oxide.

6. The oxidative coupling catalyst of claim 1 wherein the reducible compound is lead oxide.

7. The oxidative coupling catalyst of claim 1 wherein the support is silica.

8. The oxidative coupling catalyst of claim 1 wherein the silica has a surface area of from about 21 to about 75 m$^2$/gm.

9. The oxidative coupling catalyst of claim 1 wherein the support is calcined at a temperature of from about 800° C. to about 1100° C. for from about 2 hrs. to about 36 hrs. before the reducible metal compound is incorporated into it.

10. The oxidative coupling catalyst of claim 9 wherein the support is calcined at a temperature of from about 950° C. to about 1050° C. for from about 4 hrs. to about 16 hrs. before the reducible metal compound is incorporated into it.

11. The oxidative coupling catalyst of claim 1 wherein the support containing the reducible metal compound is calcined at a temperature of from about 500° C. to about 1050° C. for from about 2 hrs. to about 36 hrs.

12. The oxidative coupling catalyst of claim 11 wherein the support containing the reducible metal compound is calcined in air at a temperature of from about 950° C. to about 1050° C. for from about 4 hrs. to about 20 hrs.

13. The oxidative coupling catalyst of claim 1 comprising additionally an alkali metal component at a level of from about 0.1 to about 6 weight percent calculated as the alkali metal oxide and based on the weight of the catalyst.

14. The oxidative coupling catalyst of claim 13 wherein the alkali metal component is at a level of from about 0.5 to about 3 weight percent, calculated as the alkali metal oxide and based on the weight of the catalyst.

* * * * *

UNITED STATES PATENT AND TRADEMARK OFFICE
CERTIFICATE OF CORRECTION

PATENT NO. : 4,968,655

DATED : November 6, 1990

INVENTOR(S) : James L. Jezl, et al

It is certified that error appears in the above-identified patent and that said Letters Patent is hereby corrected as shown below:

| Col. | Line | |
|---|---|---|
| 1 | 5 | "a continuation, division" should be --a division-- |
| 3 | 13 | "cadmium,," should be --cadmium,-- |
| 4 | 23 | "boiling normally" should be --boiling, normally-- |
| 4 | 53 | "belowground" should be --below ground-- |
| 5 | 40 | "thereof Preferably" should be --thereof. Preferably-- |
| 6 | 37 | "catalyst of the" should be --catalyst for the-- |
| 11 | 60 | "C3" should be --$C_3$-- |
| 17 | 65 | "conditioners" should be --conditions-- |
| 17 | 68 | "CK107G" should be --CD107G-- |
| 18 | 41 | "$cm^2$/gm" should be --$m^2$/gm-- |
| 24 | 44 | "high" should be --highly-- |
| 25 | 50 | "rate" should be --ratio-- |
| 31 | 57 | "couling" should be --coupling-- |

UNITED STATES PATENT AND TRADEMARK OFFICE
CERTIFICATE OF CORRECTION

PATENT NO. : 4,968,655

DATED : November 6, 1990

INVENTOR(S) : James L. Jezl, et al

It is certified that error appears in the above-identified patent and that said Letters Patent is hereby corrected as shown below:

| Col. | Line | |
|---|---|---|
| 32 | 50-51 | "cetalysts" should be --catalysts-- |
| 33 | 39 | "-0.5 / -1.1" should be -- -0.5   -1.1-- |
| 34 | 7-8 | "N-$C_4$+  0.10  -14.5  -30.3  -37.8  -2.3" should be -- |

$\quad\quad\quad\quad$ N-$C_4$+ $\quad$ 0.10 $\quad$ 30.5 $\quad$ 17.6 $\quad$ 30 $\quad$ 30.2

$\quad\quad\quad\quad$ $C_4$+ $\quad\quad$ 0.10 $\quad$ -14.5 $\quad$ -30.3 $\quad$ -37.8 $\quad$ -2.3--

Signed and Sealed this

Seventh Day of July, 1992

Attest:

DOUGLAS B. COMER

*Attesting Officer* $\quad\quad$ *Acting Commissioner of Patents and Trademarks*